United States Patent
Ikeda et al.

(10) Patent No.: US 6,384,033 B1
(45) Date of Patent: May 7, 2002

(54) AMIDE DERIVATIVE

(75) Inventors: Kazuhito Ikeda; Tohru Tatsuno, both of Kobe; Hiroki Ogo, Takatsuki; Toshio Nishihara, Nishinomiya; Tatsuya Fujibayashi, Nishinomiya; Ryu Nagata, Nishinomiya, all of (JP)

(73) Assignee: Sumitomo Pharmaceuticals Company, Limited, Osaka (JP)

( * ) Notice: Subject to any disclaimer, the term of this patent is extended or adjusted under 35 U.S.C. 154(b) by 0 days.

(21) Appl. No.: 09/559,626

(22) Filed: Apr. 27, 2000

Related U.S. Application Data

(63) Continuation-in-part of application No. PCT/JP98/04782, filed on Oct. 22, 1998.

(30) Foreign Application Priority Data

Oct. 27, 1997 (JP) .............................. 9-311262
Jun. 4, 1998 (JP) ............................. 10-156045

(51) Int. Cl.[7] ................. A61K 31/4402; A61K 31/506; A61K 31/166
(52) U.S. Cl. ............... 514/247; 514/255.06; 514/252.1; 514/256; 514/354; 514/617
(58) Field of Search ................... 514/255.06, 252.1, 514/256, 247, 354, 617

(56) References Cited

U.S. PATENT DOCUMENTS

| | | | |
|---|---|---|---|
| 3,944,675 A | 3/1976 | Symchowicz et al. | 424/324 |
| 3,957,828 A | 5/1976 | Bauer et al. | 424/283 |
| 3,985,889 A | 10/1976 | Bauer et al. | 424/267 |
| 4,250,178 A | 2/1981 | Bucher et al. | 424/251 |
| 5,550,125 A | 8/1996 | George et al. | 514/230.5 |
| 5,563,144 A | 10/1996 | Damour et al. | 514/253 |
| 5,620,990 A | 4/1997 | Thenot et al. | 514/317 |

FOREIGN PATENT DOCUMENTS

| | | |
|---|---|---|
| EP | 0666260 A1 | 8/1995 |
| EP | 666260 B1 | 8/1995 |
| EP | 0692472 A1 | 1/1996 |
| EP | 692472 A1 | 1/1996 |
| JP | 5855461 A | 4/1983 |
| JP | 959236 A | 3/1997 |
| WO | WO8906649 A2 | 7/1989 |
| WO | WO9505175 A1 | 2/1995 |
| WO | 9505175 A1 | 2/1995 |
| WO | 9528153 A1 | 10/1995 |
| WO | WO9528153 A1 | 10/1995 |
| WO | WO9631462 A1 | 10/1996 |
| WO | 9631462 A1 | 10/1996 |

OTHER PUBLICATIONS

*Acta Pharmaceutica Sinica*, vol. 31, pp. 715–720 (1996) (Chinese w/English Abstract).
Yamamoto et al., *Kekkaku*, vol. 71, No. 3, pp. 253–258 (1996) (Japanese with English Abstract).
Hoshi et al., *Chem. Pharm. Bull.*, vol. 26, No. 1, pp. 161–165 (1978) (English with English Abstract).
Davidson et al., *J. Chem. Soc. Perkin I*, pp. 1511–1514 (1976).
Morrow et al., *J. Org. Chem*, vol. 52, No. 5, pp. 713–719 (Mar. 6, 1987).

*Primary Examiner*—Richard L. Raymond
*Assistant Examiner*—Kahsay Habte
(74) *Attorney, Agent, or Firm*—Birch, Stewart, Kolasch & Birch, LLP

(57) ABSTRACT

A compound of the formula:

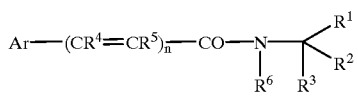

wherein
Ar is optionally substituted phenyl, etc.; n is 0, 1 or 2;
$R^1$ is hydogen atom, optionally substituted alkyl, etc.; $R^2$ and $R^3$ are independently optionally substituted alkyl, etc.;
$R^4$ and $R^5$ are independently hydrogen atom or optionally substituted alkyl; $R^6$ is hydrogen atom, hydroxy or alkyl;
or a pharmaceutically acceptable salt thereof is useful as a medicament for treating retinal degenerative disorders and the like.

20 Claims, No Drawings

AMIDE DERIVATIVE

CROSS-REFERENCE TO RELATED APPLICATION

This application is a continuation-in-part application of PCT/JP98/04782 filed on Oct. 22, 1998.

TECHNICAL FIELD

The present invention relates to amide derivatives useful as a medicament. The amide derivatives of the present invention are useful as a medicament for treating retinal neurodegenerative disorders and the like.

BACKGROUND ART

N-t-Butyl-benzamide, N-t-butyl-4-bromobenzamide, N-t-butyl-4-nitrobenzamide, etc. are known to be useful as a medicament for treating neurodegenerative disorders such as Parkinson's disease, multiple sclerosis, Alzheimer's disease and the like (WO 95/28153, WO 96/31462). N-t-Butyl-3-chloro-2-pyridinecarboxamide, N-(2-hydroxy-1,1-dimethylethyl)-6-chloro-2-pyridinecarboxamide, etc. are known to be useful as a herbicide (JP 48-26918(A), JP 60-72803(A), JP 61-151174(A)).

It has been known that N-t-butyl-4-fluorobenzamide, N-t-butyl-2-fluorobenzamide, N-(2-hydroxy-1,1-dimethylethyl)-2,4,5-trifluorobenzamide, N-(2-hydroxy-1,1-dimethylethyl)-2,5-difluorobenzamide, N-(2-hydroxy-1,1-dimethylethyl)-2-fluorobenzamide, N-(2-hydroxy-1,1-dimethylethyl)-5-chloro-2-fluorobenzamide, N-(2-hydroxy-1,1-dimethylethyl)-2-fluoro-6-iodobenzamide, N-(2-hydroxy-1,1-dimethylethyl)-2,6-difluorobenzamide, N-(2-hydroxy-1,1-dimethylethyl)-2-chloro-4-fluorobenzamide, etc. were produced as synthetic intermediates (EP 511073, WO 89/06649, J. Org. Chem., 52, 713(1987), J. Org. Chem., 53, 345(1988), EP 538231, U.S. Pat. No. 3,985,889, etc.).

However, these documents do not disclose that the amide derivatives are effective for treating retinal neurodegenerative disorders.

DESCRIPTION OF THE INVENTION

The present invention is intended to provide a medicament for treating retinal neurodegenerative disorders and the like.

The inventors of the present invention have intensively carried out research, and found that amide derivatives are useful as a medicament for treating retinal degenerative disorders and the like. Thus, the present invention has been accomplished.

The present inventions are as follows:

[1] a medicament for treating retinal neurodegenerative disorder comprising a compound of the formula:

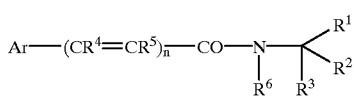

wherein
Ar is optionally substituted phenyl or optionally substituted aromatic heterocyclic group;
n is 0, 1 or 2;
$R^1$ is hydogen atom, optionally substituted alkyl, optionally substituted alkenyl, optionally substituted alkynyl, alkoxycarbonyl, carbamoyl, alkanoyl or cyano; $R^2$ and $R^3$ are independently optionally substituted alkyl; or any two groups of $R^1$, $R^2$ and $R^3$ may be taken together with the carbon atom adjacent thereto to form cycloalkane, or all of $R^1$, $R^2$ and $R^3$ may be taken together with the carbon atom adjacent thereto to form bicycloalkane or tricycloalkane, wherein the cycloalkane, the bicycloalkane and the tricycloalkane may be substituted optionally;
$R^4$ and $R^5$ are independently hydrogen atom or optionally substituted alkyl;
$R^6$ is hydrogen atom, hydroxy or alkyl;

or a pharmaceutically acceptable salt thereof;

[2] a medicament comprising a compound of the formula:

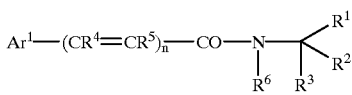

wherein
$Ar^1$ is phenyl substituted by fluorine atom at the 2 or 4 position which may be substituted by further 1 or 2 halogen atoms, or optionally substituted 6-membered heteroaryl;
n, $R^1$, $R^2$, $R^3$, $R^4$, $R^5$ and $R^6$ are as defined above;

or a pharmaceutically acceptable salt thereof; and

[3] a compound of the formula:

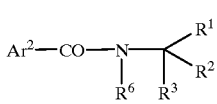

wherein
$Ar^2$ is a group of the formula:

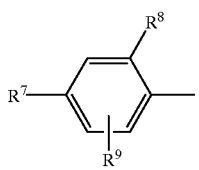

or 6-membered heteroaryl substituted by 1 to 3 halogen atoms;
n, $R^1$, $R^2$, $R^3$ and $R^6$ are as defined above; one of $R^7$ and $R^8$ is fluorine atom; the other is hydrogen atom or halogen atom;
$R^9$ is hydrogen atom or halogen atom; provided that the compound is not the following compound:

N-t-butyl-4-fluorobenzamide,
N-t-butyl-2-fluorobenzamide,
N-(2-hydroxy-1,1-dimethylethyl)-2,4,5-trifluorobenzamide,
N-(2-hydroxy-1,1-dimethylethyl)-2,5-difluorobenzamide,
N-(2-hydroxy-1,1-dimethylethyl)-2-fluorobenzamide,
N-(2-hydroxy-1,1-dimethylethyl)-5-chloro-2-fluorobenzamide,
N-(2-hydroxy-1,1-dimethylethyl)-2-fluoro-6-iodobenzamide,
N-(2-hydroxy-1,1-dimethylethyl)-2,6-difluorobenzamide,
N-(2-hydroxy-1,1-dimethylethyl)-2-chloro-4-fluorobenzamide, N-t-Butyl-3-chloro-2-pyridinecarboxamide and
N-(2-hydroxy-1,1-dimethylethyl)-6-chloro-2-pyridinecarboxamide,
or a pharmaceutically acceptable salt thereof.

"Aromatic heterocyclic group" includes, for example, 5- or 6-membered aromatic heterocyclic group containing 1 to 3 atoms selected independently from the group consisting of nitrogen atoms, sulfur atoms and oxygen atoms, and the like. Nitrogen atom or sulfur atom constituting heteroaryl may be oxidized. 5-Membered aromatic heterocyclic group includes, for example, the 5-membered aromatic heterocyclic group containing 1 or 2 atoms selected independently from the group consisting of nitrogen atoms, sulfur atoms and oxygen atoms, such as pyrrolyl, thienyl, furyl, imidazolyl, pyrazolyl, isothiazolyl, isoxazolyl, thiazolyl, oxazolyl and the like, and the like. 6-Membered aromatic heterocyclic group includes, for example, the 6-membered aromatic heterocyclic group containing 1 to 3 nitrogen atoms, and the like. Typical examples are pyridyl, 1-oxido-pyridyl, pyrazinyl, pyrimidinyl, pyridazinyl, triazinyl and the like.

"Heterocyclic group" includes aromatic heterocyclic group, aliphatic heterocyclic group and the like. Aliphatic heterocyclic group includes, for example, 5- or 6-membered aliphatic heterocyclic group containing 1 to 3 atoms selected independently from the group consisting of nitrogen atoms, sulfur atoms and oxygen atoms, and the like. 5-Membered aliphatic heterocyclic group includes, for example, the 5-membered aliphatic heterocyclic group containing 1 or 2 atoms selected independently from the group consisting of nitrogen atoms, sulfur atoms and oxygen atoms, such as pyrrolidinyl, pyrrolinyl, imidazolidinyl, pyrazolidinyl, tetrahydrofuryl, tetrahydrothienyl, dioxolanyl and the like, and the like. 6-Membered aliphatic heterocyclic group includes, for example, the 6-membered aliphatic heterocyclic group containing 1 or 2 atoms selected independently from the group consisting of nitrogen atoms, sulfur atoms and oxygen atoms, such as piperidyl, piperazinyl, morpholinyl, tetrahydropyranyl, dioxanyl and the like, and the like.

The substituent of the substituted phenyl, the substituted aromatic heterocyclic group, the substituted 5-membered aromatic heterocyclic group and the substituted 6-membered aromatic heterocyclic group may be one or more and includes, for example, halogen atom, cyano, nitro, alkyl, alkyl substituted by halogen atom(s), alkoxy, alkoxy substituted by halogen atom(s), alkoxycarbonyl, alkanoylamino, amino, phenyl, alkyl aminocarbonylamino, alkoxycarbonylamino, alkylsulfonylamino, carbamoyl, carbamoyl substituted by alkyl(s) and the like.

Preferable substituents of the substituted phenyl include, for example, halogen atom, cyano, nitro, alkyl substituted by halogen atom(s), alkoxy substituted by halogen atom(s), alkoxycarbonyl, alkanoylamino, amino, phenyl, alkylaminocarbonylamino, alkoxycarbonylamino, alkylsulfonylamino, carbamoyl, carbamoyl substituted by alkyl(s) and the like. More preferable examples are the electron-withdrawing groups such as halogen atom, cyano, nitro, trifluoromethyl and the like. Furthermore, preferable is halogen atom, and the most preferable is fluorine atom.

Preferable substituents of the substituted aromatic heterocyclic group, the substituted 5-membered aromatic heterocyclic group and the substituted 6-membered aromatic heterocyclic group include, for example, halogen atom, cyano, nitro, alkyl, alkyl substituted by halogen atom(s), alkoxycarbonyl, alkanoylamino, amino, phenyl, alkylaminocarbonylamino, alkoxycarbonylamino, alkylsulfonylamino, carbamoyl, carbamoyl substituted by alkyl(s) and the like. Particularly preferable is halogen atom.

The number of substituents of the substituted phenyl may be 1, 2 or 3. Preferable examples are 1 and 2, and more preferable is 2. Preferable position of the substitution is the 4 position, and the positions are the 2 and 4 positions if the phenyl is substituted by multiple substituents. The number of substituents of the substituted aromatic heterocyclic group, the substituted 5-membered aromatic heterocyclic group and the substituted 6-membered aromatic heterocyclic group may be 1, 2 or 3. Preferable examples are 1 and 2, and more preferable is 1.

"Alkyl" includes straight or branched $C_1$–$C_6$ alkyl. Typical examples are methyl, ethyl, propyl, 1-methylethyl, butyl, 2-methylpropyl, pentyl, 1,2-dimethylpropyl, hexyl, 3-methylpentyl and the like.

"Alkoxy" includes straight or branched $C_1$–$C_6$ alkoxy. Typical examples are methoxy, ethoxy, propoxy, 1-methylethoxy, butoxy, 2-methylpropoxy, pentyloxy, 1,2-dimethylpropoxy, hexyloxy, 3-methylpentoxy and the like.

"Alkoxyalkoxy" is the alkoxy substituted by alkoxy.
"Alkoxycarbonyl" is the carbonyl substituted by alkoxy.
"Alkyl substituted by halogen atom(s)" and "alkoxy substituted by halogen atom(s)" are the alkyl and alkoxy substituted by one halogen atom or more. Typical examples are trifluoromethyl, trifluoromethoxy and the like.

"Alkenyl" includes straight or branched alkenyl having 6 carbon atoms or less. Typical examples are vinyl, allyl, 1-propenyl, 2-butenyl, 5-hexenyl and the like.

"Alkynyl" includes straight or branched alkynyl having 6 carbon atoms or less. Typical examples are ethynyl, propargyl, 2-butynyl, 5-hexynyl and the like.

"Alkanoyl" includes, for example, straight or branched alkanoyl having 6 carbon atoms or less. Typical examples are formyl, acetyl, propionyl, butyryl, isobutyryl, valeryl, isovaleryl, pivaloyl, 2-methylbutyryl, hexanoyl and the like.

"Cycloalkyl" includes, for example, $C_3$–$C_8$ cycloalkyl. Typical examples are cyclopropyl, cyclobutyl, cyclopentyl, cyclohexyl, cycloheptyl, cyclooctyl and the like.

In the carbamoyl substituted by alkyl(s), the carbamoyl may be substituted independently by 1 or 2 alkyls.

"Halogen atom" includes, for example, fluorine atom, chlorine atom, bromine atom, iodine atom and the like. Preferable examples are fluorine atom, chlorine atom and bromine atom, and particularly preferable is fluorine atom.

"Cycloalkane" includes, for example, $C_3$–$C_8$ cycloalkane. Typical examples are cyclopropane, cyclobutane, cyclopentane, cyclohexane, cycloheptane, cyclooctane and the like.

"Bicycloalkane" includes, for example, $C_7$–$C_{10}$ bicycloalkane. Typical examples are bicyclo[2.2.1]heptane, bicyclo[2.2.2]octane and the like.

"Tricycloalkane" includes, for example, $C_7$–$C_{13}$ tricycloalkane. Typical examples are adamantane and the like.

Substituents of the substituted alkyl, the substituted alkenyl, the substituted alkynyl, the substituted cycloalkane, the substituted bicycloalkane and the substituted tricycloalkane include, for example, cycloalkyl, alkoxy, hydroxy, halogen atom, alkoxyalkoxy, alkanoyloxy, amino, alkylamino, dialkylamino, alkanoylamino, heterocyclic group such as pyrrolidino, piperidino, piperazino, 4-alkylpiperazino, morpholino and the like, and the like. Alkyl, alkenyl, alkynyl, cycloalkane, bicycloalkane and tricycloalkane may be substituted independently by one or more substituents.

Preferable examples of $R^1$, $R^2$ and $R^3$ as indicated in formulae 1, 2 and 3 are optionally substituted alkyl. More preferable are alkyl optionally substituted by hydroxy, and particularly preferable are methyl, ethyl, hydroxymethyl and hydroxyethyl.

Preferable example of $R^6$ as indicated in formulae 1, 2 and 3 is hydrogen atom.

Preferable examples of n as indicated in formulae 1 and 2 are 0 and 1, and particularly preferable is 0.

The pharmaceutically acceptable salts include, for example, salts with inorganic acids and salts with organic acids. Examples of the inorganic acids include hydrochloric acid, hydrobromic acid, hydroiodic acid, sulfuric acid and the like. Examples of the organic acids include acetic acid, oxalic acid, citric acid, malic acid, tartaric acid, maleic acid, fumaric acid and the like. The compounds of formula 1, 2 or 3 and the pharmaceutically acceptable salts thereof include their solvates such as the hydrate and the like. The compounds of formula 1, 2 or 3 include their tautomers if the tautomers exist. The compounds of formula 1, 2 or 3 include the mixture of their geometrical isomers and the isolated isomer if the geometrical isomers exist.

The compound of formula 1, 2 or 3 can be produced, for example, by the following methods. In the following description, the production process is illustrated with the compound of formula 1 as a representative.

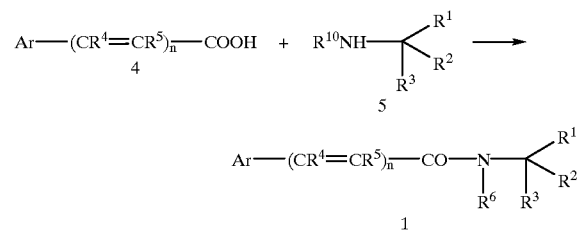

wherein $R^{10}$ is hydrogen atom, protected hydroxy or alkyl; Ar, n, $R^1$, $R^2$, $R^3$, $R^4$, $R^5$ and $R^6$ are as defined above.

Protective groups in the protected hydroxy of $R^{10}$ include conventionally used protective groups (e.g. "Protective Groups in Organic Synthesis" T. W. Greene, P. M. Wuts John. Wiley and sons 1991, pp. 10–142). Typical examples are substituted silyl such as trimethylsilyl, triisopropylsilyl, dimethylisopropylsilyl, diethylisopropylsilyl, t-butyldimethylsilyl, diphenylmethylsilyl, t-butyldiphenylsilyl and the like; optionally substituted alkyl such as t-butyl, benzyl, trityl, methoxymethyl, methylthiomethyl, benzyloxymethyl, methoxyethoxymethyl, tetrahydropyranyl and the like, and the like. Preferable are t-butyl, benzyl, trityl, methoxymethyl, tetrahydropyranyl, benzyloxymethyl, methoxyethoxymethyl and the like.

Condensation reaction of the compound of formula 4 and the compound of formula 5 can be carried out by conventional methods in peptide chemistry ("Basis and Experiment in Peptide Synthesis" by Nobuo Izumiya et. al., Maruzen, etc.). Typical methods are C-terminal activation methods (e.g. acid halide methods, acid azide methods, mixed acid anhydride methods, activated ester methods, symmetrical acid anhydride methods and the like), methods using coupling agents (e.g. methods using N,N'-dicyclohexylcarbodiimide and the like), N-terminal activation methods (e.g. isocyanate methods, phosphazo methods, phosphorous ester methods and the like) and the like.

Acid halide methods can be performed, for example, by converting the compound of formula 4 to an acid halide by a conventional method, followed by condensing with the compound of formula 5 in the presence of a base in an inert solvent such as methylene chloride and the like at 0° C. to room temperature. The bases include, for example, organic bases such as triethylamine and the like.

Methods using coupling agents can be performed, for example, by condensing the compound of formula 4 with the compound of formula 5 in the presence of coupling agents such as N-(3-dimethylaminopropyl)-N'-ethylcarbodiimide hydrochloride (WSC HCl) and the like, if desired, in the presence of 1-hydroxybenzotriazole (HOBt), in an inert solvent such as methylene chloride, N,N-dimethylformamide (DMF) and the like at 0° C. to room temperature. When Ar is optionally substituted pyridyl, the corresponding N-oxide compound can be prepared by oxidation with suitable oxidizing agents after condensation of the compound of formula 4 and the compound of formula 5. The oxidation can be performed by using an oxidizing agent such as hydrogen peroxide and the like in a solvent such as acetic acid, trifluoroacetic acid and the like at room temperature to temperature of reflux.

When $R^{10}$ is protected hydroxy, the protecting group can be removed by a conventional method. When the protecting group is t-butyl, benzyl, trityl, methoxymethyl, tetrahydropyranyl, benzyloxymethyl, methoxyethoxymethyl and the like, it can be removed by hydrogenation or hydrolysis using an acid catalyst.

The compound of formula 1, 2 or 3 can be purified by a conventional method such as column chromatography, recrystallization and the like. Recrystallization solvent includes, for example, alcohol such as methanol, ethanol, 2-propanol and the like; ether such as diethyl ether and the like; ester such as ethyl acetate and the like; aromatic solvent such as toluene and the like; ketone such as acetone and the like; hydrocarbon solvent such as hexane and the like; water and the like; and mixture thereof. Pharmaceutically acceptable salt of the compound of formula 1, 2 or 3 can be formed by conventional methods, and the salt may be purified by recrystallization or the like.

The compound of formula 1, 2 or 3 or the pharmaceutically acceptable salt thereof may be administered orally or parenterally (e.g. intramuscular injection, intravenous injection, rectal administration by suppository, dermal application for liniments, eye drops or the like). Pharmaceutical forms for oral administration include, for example, tablets, capsules, syrups, suspensions and the like. Pharmaceutical forms for injection include, for example, solutions, emulsions, suspensions and the like. These compositions can be prepared by mixing the active compound with conventional carriers, excipients, binders, stabilizers and the like by conventional methods. Injection may contain buffers, solubilizers, agents for influencing osmotic pressure and the like.

Though the dose and the times for administration varies depending on the grade of the symptoms, the patient's age, body weight, administration route and the like, the compound is usually administered to an adult in a dose of approximately 1–1000 mg, preferably 10–500 mg per day in one portion or several portions, by the oral route. By injection, the compound is usually administered to an adult in a dose of approximately 0.1–500 mg, preferably 3–100 mg per day in one portion or several portions.

Eye drops can be formed into various formulations. The examples of the eye drops are described in "Tenganzai" written by Kenji MOTOSE (published by Nanzando, 1984) and "Shin-Sogoyakuzaigaku II" edited by Sadao IGUCHI, pp. 77–91 (published by Ishiyaku-Shuppan, 1982). Typical examples of the eye drops include aqueous eye drops (aqueous eye drop solution, sticky eye drop solution, aqueous eye drop suspension, etc.) and non-aqueous eye drops (non-aqueous eye drop solution, non-aqueous eye drop suspension, ophthalmic ointment, etc.) and so on.

Eye drops can be added to by conventional additives, if necessary. Examples of the additive include buffer agents, tonicity agents, thickening agents, preservatives, solubilizing agents, suspending agents, ointment bases, non-aqueous solvents, pH adjusting agents and so on.

Examples of the buffer agents include boric acid, sodium dihydrogenphosphate, disodiumhydrogenphosphate, borax, sodium carbonate, sodium hydrogencarbonate, citric acid, sodium citrate, acetic acid, sodium acetate, sodium carbonate and so on.

Examples of the tonicity agents include sodium chloride, boric acid, sodium nitrate, potassium nitrate, potassium chloride and so on.

Examples of the thickening agents include methylcellulose, hydroxypropylmethylcellulose, polyvinyl alcohol, hydroxyethylcellulose, chondroitin sulfuric acid, polyvinylpyrrolidone, gelatine, glycerin, macrogolum and so on.

Examples of the preservatives include benzalkonium chloride, phenymercuric nitrate, phenymercuric acetate, thimerosal, chlorhexidine acetate, chlorobutanol, phenylethyl alcohol, paraoxybenzoate esters, sodium dehydroacetate, cetylpyridinium chloride, alkylpolyaminoethylglycine, sorbic acid and its salts and so on.

Examples of the solubilizing agents include sodium carboxymethylcellulose, polyoxyethylene lauryl ether, polyoxyethylene oleyl ether, polyethylene glycol monolaurate, polyethylene glycol monooleate and so on.

Examples of the suspending agents include polysorbate 80, aluminum monostearate and so on.

Examples of the ointment bases include vaseline, purified lanolin, zeren, plastibase and so on.

Examples of the non-aqueous solvents include vegetable oil, liquid paraffin, propylene glycol, mineral oil, β-octyldodecanol and so on.

Examples of the pH adjusting agents include sodium hydroxide, potassium hydroxide, sodium carbonate, hydrochloric acid, citric acid, phosphoric acid, acetic acid and so on.

Though the usage and dose of the eye drops of the invention varies depending on the concentration of the medicament, the patient's symptoms and age and so on, the eye drops are usually administered in 1 to 2 drops per one time and 1 to 6 times per day. A suitable amount of ophthalmic ointment is usually applied in saccus conjunctivae in 1 to 2 times per day.

EXAMPLES

The present invention will be described in detail below, referring to examples, which are not limitative of the present invention.

The following compounds are shown as examples of the present invention:

N-t-butyl-2-fluoro-4-bromobenzamide,
N-t-butyl-2-fluoro-4-trifluoromethylbenzamide,
N-t-butyl-2-fluoro-4-cyanobenzamide,
N-t-butyl-2-fluoro-4-nitrobenzamide,
N-t-butyl-2-fluoro-4-methanesulfonylaminobenzamide,
N-t-butyl-2-fluoro-4-phenylbenzamide,
N-t-butyl-2-fluoro-4-trifluoromethoxybenzamide,
N-t-butyl-3-fluoro-4-chlorobenzamide,
N-t-butyl-3-fluoro-4-bromobenzamide,
N-t-butyl-3-fluoro-4-trifluoromethylbenzamide,
N-t-butyl-3-fluoro-4-cyanobenzamide,
N-t-butyl-3-fluoro-4-nitrobenzamide,
N-t-butyl-6-chloro-nicotinamide,
N-t-butyl-5-chloro-2-thiophenecarboxamide,
N-t-butyl-4-chloro-2-thiophenecarboxamide,
N-t-butyl-3-fluoro-4-chlorobenzamide,
N-t-butyl-2,4-difluorobenzamide,
N-(2-hydroxy-1,1-dimethylethyl)-2,4-difluorobenzamide,
N-(2-hydroxy-1,1-dimethylethyl)-2,4,5-trifluorobenzamide,
N-(2-hydroxy-1,1-dimethylethyl)-6-chloro-3-pyridazinecarboxamide,
N-t-butyl-5-chloro-2-pyridinecarboxamide,
N-(2-hydroxy-1,1-dimethylethyl)-5-chloro-2-pyridinecarboxamide,
N-t-butyl-1-oxido-5-chloro-2-pyridinecarboxamide,
N-t-butyl-1-oxido-2-pyridinecarboxamide,
N-(2-hydroxy-1,1-dimethylethyl)-1-oxido-5-chloro-2-pyridinecarboxamide,
N-(2-hydroxy-1,1-dimethylethyl)-6-chloro-3-pyridazinecarboxamide,
N-(2-hydroxy-1,1-dimethylethyl)-3-fluoro-2-pyridinecarboxamide,
N-(2-hydroxy-1,1-dimethylethyl)-5-fluoro-2-pyridinecarboxamide,
N-(2-hydroxy-1,1-dimethylethyl)-6-chloronicotinamide,
N-t-butyl-pyrazinecarboxamide,
N-(2-hydroxy-1,1-dimethylethyl)-pyrazinecarboxamide,
N-t-butyl-4-pyridazinecarboxamide,
N-(2-hydroxy-1,1-dimethylethyl)-4-pyridazinecarboxamide,
N-(2-hydroxy-1,1-dimethylethyl)-2-pyrimidinecarboxamide, and
N-(2-hydroxy-1,1-dimethylethyl)-4-bromo-2-pyrimidinecarboxamide.

Example 1

N-t-Butyl-2,4-difluorobenzamide

A solution of t-butylamine (0.2962 g, 4.05 mmol) and triethylamine (0.70 ml, 5.02 mmol) in dichloromethane (2 ml) was cooled to 0° C. in an ice-bath. To the above solution was added a solution of 2,4-difluorobenzoyl chloride (0.3652 g, 2.07 mmol) in dichloromethane (3 ml) dropwise and stirred for 2.5 hours. The mixture was added to saturated aqueous $NaHCO_3$ and extracted three times with ethyl acetate. The combined extracts were washed with saturated aqueous $NaHCO_3$ and dried over $MgSO_4$. The solvent was evaporated to give the title compound (0.4086 g; 93%).

$^1$H-NMR(270 MHz, $CDCl_3$) 8.08 (td, 1H, J=8.9, 6.6 Hz), 7.02–6.93 (m, 1H), 6.84 (ddd, 1H, J=11.9, 8.6, 2.6 Hz), 6.5 (br, s, 1H), 1.47 (s, 9H)

Example 2

N-t-Butylbenzamide

The title compound (0.3028 g; 84%) was prepared by the same method as that described in Example 1, using benzoyl chloride (0.2851 g, 2.03 mmol).

$^1$H-NMR(270 MHz, $CDCl_3$) 7.74–7.70 (m, 2H), 7.48–7.37 (m, 3H), 5.94 (br, 1H), 1.48 (s, 9H)

Example 3

N-t-Butyl-3,4-difluorobenzamide

The title compound (0.3867 g; 90%) was prepared by the same method as that described in Example 1, using 3,4-difluorobenzoyl chloride (0.3563 g, 2.02 mmol).

$^1$H-NMR(270 MHz, CDCl$_3$) 7.58 (ddd, 1H, J=10. 9, 7.6, 2.3 Hz), 7.48–7.41 (m, 1H), 7.19 (ddd, 1H, J=9.6, 8.5, 7.7 Hz), 5.84 (br, 1H), 1.47 (s, 9H)

Example 4

N-t-Butyl-3,5-difluorobenzamide

The title compound (0.3996 g; 93%) was prepared by the same method as that described in Example 1, using 3,5-difluorobenzoyl chloride (0.3555 g, 2.01 mmol).

$^1$H-NMR(270 MHz, CDCl$_3$) 7.26–7.19 (m, 2H), 6.92 (tt, 1H, J=8.6, 2.3 Hz), 5.82 (br, 1H), 1.47 (s, 9H)

Example 5

N-t-Butyl-2, 6-difluorobenzamide

The title compound (0.4130 g; 97%) was prepared by the same method as that described in Example 1, using 2,6-difluorobenzoyl chloride (0.3547 g, 2.01 mmol).

$^1$H-NMR(270 MHz, CDCl$_3$) 7.38–7.29 (m, 1H), 6.92 (dd, 2H, J=8.4, 7.6 Hz), 5.79 (br, 1H), 1.47 (s, 9H)

Example 6

N-t-Butyl-4-fluorobenzamide

The title compound (0.3767 g; 96%) was prepared by the same method as that described in Example 1, using 4-fluorobenzoyl chloride (0.3165 g, 2.00 mmol).

$^1$H-NMR(270 MHz, CDCl$_3$) 7.72 (dd, 2H, J=9.2, 5.3 Hz), 7.09 (t, 2H, J=8.6 Hz), :5.86 (br, 1H), 1.47 (s, 9H)

Example 7

N-t-Butyl-4-bromobenzamide

The title compound (0.4794 g; 95%) was prepared by the same method as that described in Example 1, using 4-bromobenzoyl chloride (0.4301 g, 1.97 mmol).

$^1$H-NMR(270 MHz, CDCl$_3$) 7.59 (d, 2H, J=8.9 Hz), 7.54 (d, 2H, J=8.9 Hz), 5.88 (br, 1H), 1.47 (s, 9H)

Example 8

N-t-Butyl-4-methylbenzamide

The title compound (0.3611 g; 93%) was prepared by the same method as that described in Example 1, using 4-methylbenzoyl chloride (0.3153 g, 2.04 mmol).

$^1$H-NMR(270 MHz, CDCl$_3$) 7.61 (d, 2H, J=8.2 Hz), 7.21 (d, 2H, J=8.2 Hz), 5.91 (br, 1H), 2.38 (s, 3H), 1.47 (s, 9H)

Example 9

N-t-Butyl-2,4-dichlorobenzamide

The title compound (0.5017 g; >99%) was prepared by the same method as that described in Example 1, using 2,4-dichlorobenzoyl chloride (0.4169 g, 1.99 mmol).

$^1$H-NMR (270 MHz, CDCl$_3$) 7.57 (d, 1H, J 8. 1 Hz), 7.40 (d, 1H, J=2.0 Hz), 7.29 (dd, 1H, J=8.1, 2.0 Hz), 5.92 (br, 1H), 1.47 (s, 9H)

Example 10

N-t-Butyl-4-nitrobenzamide

The title compound (1.0567 g; 94%) was prepared by the same method as that described in Example 1, using 4-nitrobenzoyl chloride (0.9356 g, 5.04 mmol).

$^1$H-NMR(270 MHz, CDCl$_3$) 8.28 (d, 2H, J=8.9 Hz), 7.88 (d, 2H, J=8.9 Hz), 5.96 (br, 1H), 1.50 (s, 9H)

Example 11

N-t-Butyl-4-aminobenzamide

Ten percent Pd/C (0.1003 g) was added to a solution of N-t-butyl-4-nitrobenzamide (0.7349 g, 3.31 mmol) in ethyl acetate (10 ml), and stirred under a hydrogen atmosphere for 1 hour. The reaction mixture was filtered through Celite® bed and the solvent was evaporated. The residue was purified by silica gel chromatography (hexane/ethyl acetate/triethylamine=50/100/1) to give the title compound (0.6156 g; 97%).

$^1$H-NMR(270 MHz, CDCl$_3$) 7.55 (d, 2H, J=8.7 Hz), 6.65 (d, 2H, J=8.7 Hz), 5.81 (br, 1H), 3.92 (br, 2H), 1.45 (s, 9H)

Example 12

N-t-Butyl-4-chlorobenzamide

The title compound (0.4204 g; 99%) was prepared by the same method as that described in Example 1, using 4-chlorobenzoyl chloride (0.3507 g, 2.00 mmol).

$^1$H-NMR(270 MHz, CDCl$_3$) 7.65 (d, 2H, J=8.6 Hz), 7.38 (d, 2H, J=8.6 Hz), 5.88 (br, 1H), 1.47 (s, 9H)

Example 13

N-t-Butyl-4-methoxybenzamide

The title compound (0.4104 g; 98%) was prepared by the same method as that described in Example 1, using 4-methoxybenzoyl chloride (0.3444 g, 2.02 mmol).

$^1$H-NMR(270 MHz, CDCl$_3$) 7.68 (d, 2H, J=8.9 Hz), 6.90 (d, 2H, J=8.9 Hz), 5.87 (br, 1H), 3.84 (s, 3H), 1.47 (s, 9H)

Example 14

N-t-Butyl-4-chloro-2-fluorobenzamide

To a suspension of 4-chloro-2-fluorobenzoic acid (0.3494 g, 2.00 mmol) in methylene chloride (10 ml) were added t-butyl amine (0.32 ml, 3.05 mmol) and HOBt (0.3248 g, 2.40 mmol), and then WSC HCl (0.4596 g, 2.40 mmol) was added and stirred for 3 hours. The reaction mixture was added into water and extracted three times with ethyl acetate. The combined extracts were dried over MgSO$_4$. The solvent was evaporated and the residue was purified by silica gel chromatography (hexane/ethyl acetate=5/1) to give the title compound (0.4403 g; 96%).

$^1$H-NMR(270 MHz, CDCl$_3$) 8.01 (t, 1H, J=8.6 Hz), 7.24 (dd, 1H, J=8.6, 2.0 Hz), 7.13 (dd, 1H, J=11.6, 2.0 Hz), 6.50 (br, 1H), 1.47 (s, 9H)

Example 15

N-Isopropyl-2,4-difluorobenzamide

The title compound (0.3804 g; 95%) was prepared by the same method as that described in Example 1, using 2,4-difluorobenzoyl chloride (0.3532 g, 2.00 mmol) and isopropylamine (0.26 ml, 3.05 mmol).

$^1$H-NMR(270 MHz, CDCl$_3$) 8.12 (td, 1H, J=8.9, 6.6 Hz), 6.98 (tdd, 1H, J=8.9, 2.31, 1.0 Hz), 6.85 (ddd, 1H, J=12.0, 8.4, 2.3 Hz), 6.45 (br, 1H), 4.35–4.25 (m, 1H), 1.27 (d, 6H, J=6.6 Hz)

Example 16

N-t-Butyl-4-methoxycarbonylbenzamide

The title compound (0.2134 g; 39%) was prepared by the same method as that described in Example 1, using 4-methoxycarbonylbenzoyl chloride (0.3933 g, 1.98 mmol).

¹H-NMR(270 MHz, CDCl₃) 8.08 (d, 2H, J=8.7 Hz), 7.77 (d, 2H, J=8.7 Hz), 5.95 (br, 1H), 3.94 (s, 3H), 1.48 (s, 9H)

Example 17

N-t-Butylisonicotinamide

The title compound (0.3017 g; 84%) was prepared by the same method as that described in Example 1, using isonicotinoyl chloride hydrochloride (0.3606 g, 2.02 mmol).
¹H-NMR(270 MHz, CDCl₃) 8.72 (dd, 2H, J=4.3, 1.7 Hz), 7.56 (dd, 2H, J=4.3, 1.7 Hz), 5.95 (br, 1H), 1.48 (s, 9H)

Example 18

N-t-Butyl-2-chloro-4-fluorobenzamide

The title compound (0.4278 g; 93%) was prepared by the same method as that described in Example 14, using 2-chloro-4-fluorobenzoic acid (0.3492 g, 2.00 mmol).
¹H-NMR(270 MHz, CDCl₃) 7.64 (dd, 1H, J=8.6, 6.3 Hz), 7.12 (dd, 1H, J=8.6, 2.4 Hz), 7.03 (td, 1H, J=8.6, 2.4 Hz), 5.91 (br, 1H), 1.47 (s, 9H)

Example 19

N-t-Butyl-3-thiophenecarboxamide

The title compound (0.1856 g; 51%) was prepared by the same method as that described in Example 14, using 3-thiophenecarboxylic acid (0.2567 g, 2.00 mmol).
¹H-NMR(270 MHz, CDCl₃) 7.77 (dd, 1H, J=2.6, 1.7 Hz), 7.33 (dd, 1H, J=5.2, 2.6 Hz), 7.31 (dd, 1H, J=5.2, 1.7 Hz), 5.76 (br, 1H), 1.46 (s, 9H)

Example 20

N-t-Butylnicotinamide

The title compound (0.2966 g; 83%) was prepared by the same method as that described in Example 1, using nicotinoyl chloride hydrochloride (0.3569 g, 2.00 mmol).
¹H-NMR(270 MHz, CDCl₃) 8.91 (dd, 1H, J=2.3, 0.8 Hz), 8.70 (dd, 1H, J=4.9, 1.7 Hz), 8.07 (ddd, 1H, J=7.9, 2.3, 1.7 Hz), 7.37 (ddd, 1H, J=7.9, 4.9, 0.8 Hz), 5.95 (br, 11H), 1.49 (s, 9H)

Example 21

N-t-Butylpicolinamide

The title compound (0.3109 g; 86%) was prepared by the same method as that described in Example 1, using picolinoyl chloride hydrochloride (0.3624 g, 2.04 mmol).
¹H-NMR(270 MHz, CDCl₃) 8.52 (ddd, 1H, J=4. 6, 1.7, 1.0 Hz), 8.18 (ddd, 1H, J=7.9, 1.3, 1.0 Hz), 8.00 (br, 1H), 7.83 (ddd, 1H, J=7.9, 7.6, 1.7 Hz), 7.40 (ddd, 1H, J=7.6, 4.6, 1.3 Hz), 1.50 (s, 9H)

Example 22

N-t-Butyl-2,3-difluorobenzamide

The title compound (0.3873 g; 91%) was prepared by the same method as that described in Example 14, using 2,3-difluorobenzoic acid (0.3159 g, 2.00 mmol).
¹H-NMR(270 MHz, CDCl₃) 7.76 (ddd, 1H, J=8.1, 6.6, 1.6 Hz), 7,33–7.22 (m, 1H), 7.17 (tdd, 1H, J=8.1, 4.8, 1.6 Hz), 6.43 (br, 1H), 1.48 (s, 9H)

Example 23

N-t-Butyl-2-thiophenecarboxamide

The title compound (0.3700 g; >99%) was prepared by the same method as that described in Example 1, using 2-thiophenecarbonyl chloride (0.2939 g, 2.00 mmol).
¹H-NMR(270 MHz, CDCl₃) 7.43 (dd, 1H, J=5.0, 1.0 Hz), 7.40 (dd, 1H, J=4.0, 1.0 Hz), 7.04 (dd, 1H, J=5.0, 4.0 Hz), 5.80 (br, 1H), 1.46 (s, 9H)

Example 24

N-t-Butyl-4-phenylbenzamide

The title compound (0.4869 g; 95%) was prepared by the same method as that described in Example 14, using 4-phenylbenzoic acid (0.3982 g, 2.01 mmol).
¹H-NMR (270 MHz, CDCl₃) 7.80 (d, 2H, J=9.2 Hz), 7.66–7.59 (m, 4H), 7.49–7.37 (m, 3H), 5.98 (br, 1H), 1.50 (s, 9H)

Example 25

N-t-Butyl-2,5-difluorobenzamide

The title compound (0.3921 g; 91%) was prepared by the same method as that described in Example 14, using 2,5-difluorobenzoic acid (0.3173 g, 2.01 mmol).
¹H-NMR (270 MHz, CDCl₃) 7.78–7.71 (m, 1H), 7.14–7.03 (m, 2H), 6.60 (br, 1H), 1.47 (s, 9H)

Example 26

N-(2-Fluoro-1,1-dimethylethyl)-2,4-difluorobenzamide

WSC HCl (1.15 g, 6 mmol) was added to a mixture of 2,4-difluorobenzoic acid (0.95 g, 6 mmol), 2-fluoro-1,1-dimethylethylamine hydrochloride (J. Med. Chem., 34, 29–37(1991): 0.77 g, 6 mmol), HOBt (0.81 g, 6 mmol) and triethylamine (0.91 g, 9 mmol) in methylene chloride (15 ml), and stirred at room temperature for 3 hours. The reaction mixture was concentrated, diluted with ethyl acetate and washed with saturated aqueous NaHCO₃, 1N hydrochloric acid, saturated aqueous NaHCO₃ and brine, successively, dried over MgSO₄ and concentrated under a reduced pressure. The residue was purified by silica gel chromatography (hexane/ethyl acetate=20/1) to give the title compound (0.61 g; 44%).
¹NMR(270 MHz, CDCl₃) 8.07 (1H, td, J=8.9, 6.6 Hz), 6.95–7.02 (1H, m), 6.86 (1H, ddd, J=12, 8, 3 Hz), 6.57 (1H, br), 4.56 (2H, d, J=47.5 Hz), 1.47 (6H, d, J=2 Hz)

Example 27

N-(2-Hydroxy-1,1-dimethylethyl)-2,4-difluorobenzamide

WSC HCl (7.68 g, 40 mmol) was added to a mixture of 2,4-difluorobenzoic acid (6.32 g, 40 mmol), 2-amino-2-methyl-1-propanol (3.56 g, 40 mmol) and HOBt (5.40 g, 40 mmol) in methylene chloride (150 ml), and stirred at room temperature for 3 hours. The reaction mixture was concentrated, diluted with ethyl acetate and washed with saturated aqueous NaHCO₃, 1N hydrochloric acid, saturated aqueous NaHCO₃ and brine, successively, dried over MgSO₄ and concentrated under a reduced pressure. The residue was purified by silica gel chromatography (hexane/ethyl acetate 3/1) to give the title compound (6.20 g; 68%).
¹H-NMR(270 MHz, CDCl₃) 8.08 (1H, td, J=8.8, 6.6 Hz), 6.96–7.04 (1H, m), 6.87 (1H, ₁ddd, J=12, 8, 2 Hz), 6.76 (1H, br), 4.43 (1H, t, J=6 Hz), 3.69 (2H, d, J=6 Hz), 1.42 (6H, s)

Example 28

N-(1-Cyano-1-methylethyl)-2,4-difluorobenzamide

The title compound was prepared by the same method as that described in Example 27, using 2-amino-2-methylpropionitrile (J. Med. Chem., 37, 1810–1822(1994)).

$^1$H-NMR(270 MHz, CDCl$_3$) 8.18 (1H, td, J=9.2, 6.6 Hz), 7.00–7.07 (1H, m), 6.86 (1H, ddd, J=12, 8, 2 Hz), 6.71 (1H, br), 1.82 (6H, s)

Example 29

N-(1-Carbamoyl-1-methylethyl)-2,4-difluorobenzamide

The title compound was prepared by the same method as that described in Example 26, using 2-amino-2-methylpropanamide hydrochloride.

$^1$H-NMR(270 MHz, CDCl$_3$) 8.09 (1H, td, J=8.9, 6.6 Hz), 7.28 (1H, br), 6.96–7.04 (1H, m), 6.88 (1H, ddd, J=12, 8, 2 Hz), 6.34 (1H, br), 5.54 (1H, br), 1.70 (6H, s)

Example 30

N-(1-Methoxycarbonyl-1-methylethyl)-2,4-difluorobenzamide

The title compound was prepared by the same method as that described in Example 26, using methyl 2-amino-2-methylpropionate hydrochloride.

$^1$H-NMR(270 MHz, CDCl$_3$) 8.10 (1H, td, J=9.2, 6.6 Hz), 7.22 (1H, br), 6.95–7.03 (1H, m), 6.88 (1H, ddd, J 12, 8, 2 Hz), 3.79 (3H, s), 1.67 (6H, s)

Example 31

N-(2-Methoxy-1,1-dimethylethyl)-2,4-difluorobenzamide

A solution of 2M trimethylsilyldiazomethane in hexane (3.9 ml, 7.8 mmol) was added dropwise to a solution of N-(2-hydroxy-1,1-dimethylethyl)-2,4-difluorobenzamide obtained in Example 27 (0.59 g, 2.6 mmol) and boron trifluoride diethyl etherate (43 mg, 0.3 mmol) in methylene chloride (6 ml), and stirred at room temperature overnight. To the reaction mixture was added 1N hydrochloric acid (5 ml) dropwise, and the resulting mixture was concentrated and extracted with ethyl acetate. The extract was washed with brine, dried over MgSO$_4$ and concentrated under a reduced pressure. The residue was purified by silica gel column chromatography (hexane/ethyl acetate=10/1) to give the title compound (0.38 g; 60%).

$^1$H-NMR(270 MHz, CDCl$_3$) 8.07 (1H, td, J=8.9, 6.6 Hz), 6.93–7.00 (1H, m), 6.88 (1H, br), 6.83 (1H, ddd, J=12, 8, 3 Hz), 3.44 (2H, s), 3.41 (3H, s), 1.47 (6H, s)

Example 32

N-(1-Formyl-1-methylethyl)-2,4-difluorobenzamide

To a solution of N-(2-hydroxy-1,1-dimethylethyl)-2,4-difluorobenzamide obtained in Example 27 (6.2 g, 27 mmol) and triethylamine (8.2 g, 81 mmol) in DMSO (60 ml) was added a solution of pyridine sulfur trioxide complex (12.9 g, 81 mmol) in DMSO (60 ml) dropwise with cooling in an ice-bath and stirred for 2 hours. The reaction mixture was poured over a mixture of ice and water, and extracted with ethyl acetate. The extract was washed with 1N hydrochloric acid, saturated aqueous NaHCO$_3$ and brine, successively dried over Na$_2$SO$_4$, concentrated under a reduced pressure and the residue was crystallized from hexane/ethyl acetate to give the title compound (5.05 g; 82%).

$^1$H-NMR:(270 MHz, CDCl$_3$) 9.47 (1H, s), 8.11 (1H, td, J=8.9, 6.6 Hz), 7.14 (1H, br), 61.98–7.04 (1H, m), 6.90 (1H, ddd, J=12, 8, 2 Hz), 1.51 (6H, s)

Example 33

N-(2-Hydroxy-1,1-dimethylpropyl)-2,4-difluorobenzamide

To a solution of N-(1-formyl-1-methylethyl)-2,4-difluorobenzamide obtained in Example 32 (1.14 g, 5 mmol) in THF (10 ml) was added 0.9 M methyl magnesium bromide in THF (13 ml, 12 mmol) dropwise at −20° C. The reaction mixture was warmed gradually to room temperature over 2 hours and added to 10% aqueous ammonium chloride (100 ml). The resulting mixture was extracted with ethyl acetate, washed with saturated aqueous NaHCO$_3$ and brine, dried over MgSO$_4$, concentrated under a reduced pressure and the residue was crystallized from hexane/ethyl acetate to give the title compound (1.05 g; 86%).

$^1$H-NMR(270 MHz, CDCl$_3$) 8.08 (1H, td, J=8.8, 6.6 Hz), 6.97–7.04 (1H, m), 6.87 (1H, ddd, J=12, 8, 2 Hz), 6.73 (1H, br), 4.55 (1H, br d, J=6 Hz), 3.80 (1H, m) 1.49 (3H, s), 1.37 (3H, s), 1.20 (3H, d, J=6.3 Hz)

Example 34

N-(2-Oxo-1,1-dimethylpropyl)-2,4-difluorobenzamide

To a solution of N-(2-hydroxy-1,1-dimethylpropyl)-2,4-difluorobenzamide obtained in Example 33 (0.30 g, 1.2 mmol) and triethylamine (0.37 g, 3.7 mmol) in DMSO (3 ml) was added pyridine sulfur trioxide complex (0.59 g, 3.7 mmol) portionwise and stirred at room temperature for 3 hours. The reaction mixture was added to a mixture of ice and water and extracted with ethyl acetate. The extract was washed with 1N hydrochloric acid, saturated aqueous NaHCO$_3$ and brine, successively dried over Na$_2$SO$_4$ and concentrated under a reduced pressure. The residue was crystallized from hexane/ethyl acetate to give the title compound (0.24 g; 81%).

$^1$H-NMR(270 MHz, CDCl$_3$) 8.08 (1H, td, J=8.9, 6.6 Hz), 7.47 (1H, br), 6.96–7.03 (1H, m), 6.89 (1H, ddd, J=12, 8, 2 Hz), 2.25 (3H, s), 1.61 (6H, s)

Example 35

N-(1-Carboxy-1-methylethyl)-2,4-difluorobenzamide

To a solution of N-(1-methoxycarbonyl-1-methylethyl)-2,4-difluorobenzamide obtained in Example 30 (1.51 g, 5.9 mmol) in methanol (10 ml) was added 4N aqueous NaOH (10 ml), and stirred at room temperature for 30 min. The methanol was evaporated and the resulting mixture was acidified with 4N hydrochloric acid and extracted with ethyl acetate. The extract was dried over Na$_2$SO$_4$ and the solvent was evaporated under a reduced pressure to give the title compound (1.42 g; 99%).

$^1$H-NMR(270 MHz, CDCl$_3$) 12.35 (1H, br), 8.44 (1H, br), 7.64 (1H, td, J=8.7, 6.5 Hz), 7.33 (1H, ddd, J=11, 9, 2 Hz), 7.13–7.20 (1H, m), 1.44 (6H, s)

Example 36

N-(1,1-Dimethyl-2-propynyl)-2,4-difluorobenzamide

The title compound was prepared by the same method as that described in Example 27, using 1,1-dimethylpropargylamine.

$^1$H-NMR(270 MHz, CDCl$_3$) 8.15 (1H, td, J=8.9, 7.0 Hz), 6.96–7.02 (1H, m), 6.85 (1H, ddd, J=12, 8, 2 Hz), 6.76 (1H, br), 2.40 (1H, s), 1.75 (6H, s)

Example 37

N-(1,1-Dimethyl-2-propenyl)-2,4-difluorobenzamide

Five percent Pd/BaSO$_4$ (100 mg) was added to a solution of N-(1,1-dimethyl-2-propynyl)-2,4-difluorobenzamide obtained in Example 36 (1.0 g, 4.5 mmol) and quinoline (100 mg) in methanol (20 ml), and stirred under a hydrogen atmosphere at room temperature for 1.5 hours. The catalyst was removed by filtration and the filtrate was concentrated under a reduced pressure. The residue was diluted with ethyl acetate and washed, with 1N hydrochloric acid (×3), saturated aqueous NaHCO$_3$ and brine and dried over Na$_2$SO$_4$. The solvent was evaporated and the residue was purified by silica gel column chromatography (hexane/ethyl acetate=15/1) to give the title compound (0.95 g; 94%).

$^1$H-NMR(270 MHz, CDCl$_3$) 8.09 (1H, td, J=8.9, 6.6 Hz), 6.94–7.01 (1H, m), 6.85 (1H, ddd, J=12, 8, 2 Hz), 6.66 (1H, br), 6.10 (1H, dd, J=17.5, 11 Hz), 5.18 (1H, d, J=17.5 Hz), 5.10 (1H, d, J=11 Hz), 1.55 (6H, s)

Example 38

N-(1,1-Dimethylpropyl)-2,4-difluorobenzamide

To a solution of t-amylamine (0.35 ml, 3.0 mmol) and triethylamine (0.56 ml, 4.0 mmol) in methylene chloride (3 ml) was added a solution of 2,4-difluorobenzoyl chloride (0.36 g, 2.0 mmol) in methylene chloride (2 ml) with cooling in an ice-bath, and stirred for 1 hour. The reaction mixture was poured over saturated aqueous NaHCO$_3$ and extracted with ethyl acetate. The extract was washed with saturated aqueous NaHCO$_3$ and dried over MgSO$_4$. The solvent was evaporated to give the title compound (0.47 g; >99%).

$^1$H-NMR(270 MHz, CDCl$_3$) 8.07 (td, J=9.1, 6.6 Hz, 1H), 7.01–6.93 (m, 1H), 6.84 (ddd, J=11.9, 8.6, 2.6 Hz, 1H), 6.40 (br, 1H), 1.82 (q, J=7.6 Hz, 2H), 1.41 (s, 6H), 0.91 (t, J=7.6 Hz, 3H)

Example 39

N-t-Butyl-6-chloro-3-pyridazinecarboxamide 1) 6-Chloro-3-vinylpyridazine

Pd(PPh$_3$)$_4$ (0.42 g, 0.37 mmol) was added to a suspension of tributyl(vinyl)tin (7.67 g, 24.2 mmol) and 3,6-dichloropyridazine (3.57 g, 24.0 mmol) in toluene (30 ml), and stirred at 50° C. for 8 hours. The reaction mixture was added to aqueous ammonium fluoride (100 ml), and ethyl acetate (30 ml) was added thereto and stirred for 1 hour. The white precipitates were removed by filtration. The organic layer was separated from the filtrate and the aqueous layer was extracted three times with ethyl acetate. The organic layers were combined and dried over MgSO$_4$. The solvent was evaporated and the residue was purified by silica gel chromatography (hexane/ethyl acetate=3/1) to give the title compound (1.03 g; 31%).

2) 6-Chloro-3-pyridazinecarboxylic acid

AD-mix-α (Aldrich Chemical Company: 1.39 g) was added to a mixture of t-butanol and water (1:1, 10 ml) and stirred. The mixture was cooled in an ice-bath and 6-chloro-3-vinylpyridazine (0.14 g, 1.0 mmol) was added thereto. The resulting mixture was warmed to room temperature gradually and stirred overnight. After the reaction mixture was cooled in an ice-bath, sodium sulfite (1.53 g) was added thereto and stirred for 1 hour. The reaction mixture was extracted with ethyl acetate and the extract was dried over Na$_2$SO$_4$. The solvent was evaporated and the residue was purified by silica gel chromatography (chloroform/methanol=10/1) to give the diol (0.14 g; 81%). The diol was dissolved in chloroform (3 ml), and saturated aqueous NaHCO$_3$ (0.12 ml) and sodium periodate (0.35 g, 1.6 mmol) were added thereto and stirred for 1 hour. Na$_2$SO$_4$ was added thereto and filtered off, after stirring for 1 hour. The solvent was evaporated under a reduced pressure to give 6-chloro-3-pyridazinecarboxyaldehyde (0.10 g; 90%). To an aqueous solution (2 ml) of disodium hydrogen phosphate dodecahydrate (50 mg), were added acetnitrile (3 ml), 6-chloro-3-pyridazinecarboxyaldehyde (0.10 g, 0.70 mmol), 31% aqueous hydrogen peroxide (0.12 g, 1.1 mmol) and sodium chlorite (0.10 g, 1.1 mmol), and stirred for 3 hours. The precipitated solid was removed by filtration. Water (20 ml) was added to the filtrate and the resulting mixture was extracted with ethyl acetate (30 ml×3) and the extracts were dried over Na$_2$SO$_4$. The solvent was evaporated to give the title compound (0.043 g; 39%).

$^1$H-NMR(270 MHz, DMSO-d$_6$) 8.23 (d, J=9.0 Hz, 1H), 8.09 (d, J=9.0 Hz, 1H)

3) N-t-Butyl-6-chloro-3-pyridazinecarboxamide

To a solution of 6-chloro-3-pyridazinecarboxylic acid (0.12 g, 0.76 mmol) in methylene chloride (15 ml) were added t-butylamine (0.21 ml, 2.0 mmol) and N,N-bis(2-oxo-3-oxazolidinyl)phosphinic chloride (0.24 g, 0.93 mmol), and stirred overnight. The reaction mixture was added to saturated aqueous NaHCO$_3$ and extracted three times with ethyl acetate. The combined organic layers were washed with brine and dried over Na$_2$SO$_4$. The solvent was evaporated and the residue was purified by silica gel chromatography (hexane/ethyl acetate=2/1) to give the title compound (0.080 g; 49%).

$^1$H-NMR (270 MHz, CDCl$_3$) 8.27 (d, J=8.8 Hz, 1H), 7.97 (br, 1H), 7.67 (d, J=8.8 Hz, 1H), 1.51 (s, 9H)

Example 40

N-t-Butyl-5-chloro-2-pyridinecarboxamide 1) 5-Chloro-2-vinylpyridine

Pd(PPh$_3$)$_4$ (0.46 g, 0.4 mmol) was added to a solution of tributyl(vinyl)tin (6.33 g, 20.0 mmol) and 2,5-dichloropyridine (2.96 g, 20.0 mmol) in toluene (30 ml), followed by heating under reflux for 3 hours. The reaction mixture was added to aqueous ammonium fluoride (100 ml), and ethyl acetate (30 ml) was added thereto and stirred for 1 hour. The white precipitates were removed by filtration. The organic layer was separated from the filtrate and the aqueous layer was extracted three times with ethyl acetate. The organic layers were combined and dried over Na$_2$SO$_4$. Purification through silica gel chromatography (hexane/ethyl acetate=10/1 to 2/1) followed by evaporation of the solvent at an atmospheric pressure gives the title compound (3.6 g) as an oil containing a solvent.

$^1$H-NMR(270 MHz, CDCl$_3$) 8.52 (d, J=2.4 Hz, 1H), 7.62 (dd, J=8.5, 2.4 Hz, 1H), 7.29 (d, J=8.5 Hz, 1H), 6.78 (dd, J=17.5, 10.7 Hz, 1H) , 6.18 (dd, J=17.5, 1.3 Hz, 1H), 5.51 (dd, J=10.7, 1.3 Hz, 1H)

2) 5-Chloro-2-pyridinecarboxylic acid

Potassium carbonate (0.29 g, 2.1 mmol) was added portionwise to an aqueous solution (10 ml) of sodium periodate (2.13 g, 9.98 mmol) and potassium permanganate (0.065 g, 0.41 mmol). After t-butanol (5 ml) was added, 5-chloro-2-vinylpyridine obtained above (0.34 g, ca. 2 mmol) was added portionwise followed by stirring for 1 hour. Then ethylene glycol (1 ml) was added thereto and stirred for another hour. The reaction mixture was added to 5% aqueous KHSO$_4$, extracted three times with ethyl acetate and the extracts were dried over Na$_2$SO$_4$. The solvent was evaporated to give the title compound (0.31 g).

¹H-NMR (270 MHz, DMSO-d₆) 8.76 (dd, J=2.3, 0.5 Hz, 1H), 8.12 (dd, J=8.3, 2.3 Hz, 1H), 8.04 (dd, J=8.3, 0.5 Hz, 1H)

3) N-t-Butyl-5-chloro-2-pyridinecarboxamide

The title compound was prepared by the same method as that described in Example 27, using 5-chloro-2-pyridinecarboxylic acid and t-butylamine.

¹H-NMR!(270 MHz, CDCl₃) 8.46 (dd, J=2.4, 0.6 Hz, 1H), 8.13 (dd, J=8.4, 0.6 Hz, 1H), 7.85 (br, 1H), 7.80 (dd, J=8.4, 2.4 Hz, 1H), 1.49 (s, 9H)

Example 41

N-t-Butyl-1-oxido-5-chloro-2-pyridinecarboxamide

Thirty-one percent aqueous hydrogen peroxide (1.0 ml) was added to a solution of N-t-butyl-5-chloro-2-pyridinecarboxamide obtained in Example 40 (0.35 g, 1.65 mmol) in trifluoroacetic acid (5 ml), and heated under reflux for 1.5 hours. The reaction mixture was added portionwise into an ice-cooled 1N aqueous NaOH and extracted three times with ethyl acetate and the extracts were dried over MgSO₄. The solvent was evaporated, and the residue was purified by silica gel chromatography (hexane/ethyl acetate= 5/1 to 2/1) to give the title compound (0.24 g, 65%).

¹H-NMR(270 MHz, CDCl₃) 10.90 (br, 1H), 8.35 (d, J=8.5 Hz, 1H), 8.27 (d, J=1.6 Hz, 1H), 7.43 (dd, J=8.5, 1.6 Hz, 1H), 1.47 (s, 9H)

Example 42

N-t-Butyl-3-fluoro-2-pyridinecarboxamide
1) 1-Oxido-3-fluoropyridine

Thirty-one percent aqueous hydrogen peroxide (22.2 g, 196 mmol) was added to a solution of 3-fluoropyridine (9.5 g, 98 mmol) in acetic acid (100 ml), and heated under reflux for 5 hours. The reaction mixture was allowed to cool and concentrated under a reduced pressure to about one third of its volume. Ethanol (10 ml) and water (50 ml) were added thereto and the mixture was concentrated again. The residue was basified with conc. aqueous NaOH and extracted with chloroform. The solvent was evaporated to dryness under a reduced pressure to give the title compound (9.0 g; 81%).

¹H-NMR(270 MHz, CDCl₃) 8.16 (m, 1H), 8.07 (d, J=7 Hz, 1H), 7.26 (q, J=7 Hz, 1H), 7.07 (t, J=7 Hz, 1H)

2) N-t-Butyl-3-fluoro-2-pyridinecarboxamide

Dimethyl sulfate (1.01 g, 8 mmol) was added to 1-oxido-3-fluoropyridine (0.9 g, 8 mmol) and stirred at 100° C. for 2 hours. The reaction mixture was allowed to cool and concentrated to dryness under a reduced pressure. Water (10 ml) was added to the residue and cooled in an ice-bath. Sodium cyanide (1.18 g, 24 mmol) was added to the mixture and stirred for 30 min. followed by stirring at room temperature for 30 min. Aqueous NaOH (1N) was added thereto and extracted with chloroform.

The extract was dried over Na₂SO₄ and the solvent was evaporated under a reduced pressure to give a mixture of regio-isomers of fluorocyanopyridine (0.9 g). Aqueous NaOH (4N, 10 ml) was added to the mixture of regio-isomers and heated under reflux for 2.5 hours. The mixture was allowed to cool, acidified with conc. hydrochloric acid and concentrated to dryness under a reduced pressure. The residue was suspended in DMF (10 ml), and t-butylamine (1.46 g, 20 mmol), WSC HCl (3.1 g, 16 mmol) and HOBt (2.2 g, 16 mmol) were added thereto and stirred overnight. The reaction mixture was diluted with water and extracted with ethyl acetate. The extract was washed with saturated aqueous NaHCO₃ and dried over Na₂SO₄. The solvent was evaporated under a reduced pressure and the residue was purified by silica gel chromatography (hexane/ethyl acetate= 5/1) to give the title compound (0.19 g; 12%).

¹H-NMR(270MHz, CDCl₃) 8.34 (dt, J=4, 1.3 Hz, 1H), 7.77 (br, 1H), 7.53 (ddd, J=10.5, 8.5, 1.3 Hz, 1H), 7.44 (dt, J=8.5, 4 Hz, 1H), 1.49 (s, 9H)

Example 43

N-t-Butyl-5-fluoro-2-pyridinecarboxamide
1) 5-Fluoro-2-pyridinecarboxylic acid

To water (100 ml) were added 5-fluoro-2-methylpyridine (J. Med. Chem., 32, 1970(1989): 2.2 g, 20 mmol) and potassium permanganate (19.1 g, 120 mmol), and heated under reflux for 4 hours. The reaction mixture was filtrated and the filtrate was concentrated, acidified with KHSO₄, extracted with ethyl acetate and the extract was dried over Na₂SO₄. The solvent was evaporated to give the title compound (0.80 g; 28%).

¹H-NMR(270 MHz, DMSO-d₆) 8.70 (d, J=2.8 Hz, 1H), 8.14 (dd, J=8.7, 4.6 Hz, 1H), 7.89 (td, J=8.7, 2.8 Hz, 1H)

2) N-t-Butyl-5-fluoro-2-pyridinecarboxamide

The title compound was prepared by the same method as that described in Example 39-3), using 5-fluoro-2-pyridinecarboxylic acid and t-butyl amine.

¹H-NMR(270 MHz, CDCl₃) 8.35 (d, J=2.8 Hz, 1H), 8.21 (dd, J=8.6, 4.5 Hz, 1H), 7.82 (br, 1H), 7.52 (td, J=8.6, 2.8 Hz, 1H), 1.49 (s, 9H)

Example 44

N-t-Butyl-2,4,5-trifluorobenzamide

The title compound was prepared by the same method as that described in Example 26, using 2,4,5-trifluorobenzoic acid and t-butylamine.

¹H-NMR(270 MHz, CDCl₃) 7.91 (ddd, J=11, 9, 7 Hz, 1H), 6.97 (ddd, J=11, 10, Hz, 1H), 5.53 (br, 1H), 1.46 (s, 9H)

Example 45

N-t-Butyl-1-oxido-5-fluoro-2-pyridinecarboxamide

The title compound was prepared by the same method as that described in Example 41, using N-t-butyl-5-fluoro-2-pyridinecarboxamide obtained in Example 44.

¹H-NMR(270 MHz, DMSO-d₆) 10.92 (br, 1H), 8.77 (dd, J=4. 9, 2.3 Hz, 1H), 8.25 (dd, J=9.2, 7.0 Hz, 1H), 7.63 (ddd, J=9.2, 7.0, 2.3 Hz, 1H), 1.38 (s, 9H)

Example 46

N-t-Butyl-6-chloro-3-pyridinecarboxamide

The title compound was prepared by the same method as that described in Example 26, using 6-chloronicotinic acid and t-butylamine.

¹H-NMR(270 MHz, CDCl₃) 8.67 (d, J=2.6 Hz, 1H), 8.03 (dd, J=8.3, 2.6 Hz, 1H), 7.39 (dd, J=8.3, 0.7 Hz, 1H), 5.88 (br, 1H), 1.48 (s, 9H)

Example 47

N-(2-Hydroxy-1,1-dimethylethyl)-5-chloro-2-pyridinecarboxamide

The title compound was prepared by the same method as that described in Example 26, using 5-chloro-2-pyridinecarboxylic acid obtained in Example 40-2) and 2-amino-2-methyl-1-propanol.

$^1$H-NMR (270 MHz, CDCl$_3$) 8.49 (dd, J=2. 4, 0.7 Hz, 1H), 8.14 (dd, J=8.6, 0.7 Hz, 1H), 8.05 (br, 1H), 7.83 (dd, J=8.6, 2.4 Hz, 1H), 4.70 (t, J=6.4 Hz, 1H), 3.73 (d, J=6.4 Hz, 2H), 1.43 (s, 6H)

Example 48

N-t-butyl-2-fluorobenzamide

The title compound (380 mg, 97%) was prepared by the same method as that described in Example 14, using 2-fluorobenzoic acid (280 mg, 2 mmol) in place of 4-chloro-2-fluorobenzoic acid.

$^1$H-NMR(270 MHz, CDCl$_3$) 8.05 (td, J =7.9, 2.0 Hz, 1H), 7.48–7.38 (m, 1H), 7.24 (td, J=7.9, 1.0 Hz, 1H), 7.09 (ddd, J=12, 8, 1 Hz, 1H), 6.60 (br, 1H), 1.48 (s, 9H)

Example 49

N-t-butyl-4-bromo-2-fluorobenzamide
1) 4-Bromo-2-fluorobenzoic acid

To a mixture of water (3 ml) and acetonitrile (5 ml) were added Na$_2$HPO$_4$.12H$_2$O (0.11 g), 31% aqueous hydrogen peroxide (0.34 g, 3.1 mmol), 4-bromo-2-fluorobenzaldehyde (0.41 g, 2.0 mmol) and sodium chlorite (0.27 g, 3.0 mmol), successively, and stirred at room temperature for 1 hour. The reaction solution was poured into 5% KHSO$_4$, extracted three times with ethyl acetate and the combined extracts were dried over MgSO$_4$. The solvent was evaporated under a reduced pressure to give the title compound (0.42 g; 96%).

$^1$H-NMR(270 MHz, CDCl$_3$) 7.91 (dd, J=8.4, 7.8 Hz, 1H), 7.44–7.36 (m, 2H)

2) N-t-butyl-4-bromo-2-fluorobenzamide

The title compound (0.51 g, 96%) was prepared by the same method as that described in Example 14, using 4-bromo-2-fluorobenzoic acid (0.42 g, 1.9 mmol) in place of 4-chloro-2-fluorobenzoic acid.

$^1$H-NMR(270 MHz, CDCl$_3$) 7.94 (t, J=8.3 Hz, 1H), 7.40 (dd, J=8.3, 1.8 Hz, 1H); 7.29 (dd, J=11, 2 Hz, 1H), 6.50 (br, 1H), 1.46 (s, 9H)

Example 50

N-t-butyl-1-oxide-2-pyridinecarboxamide

N-t-butyl-2-pyridinecarboxamide was prepared by the same method as that described in Example 14, using picolinic acid in place of 4-chloro-2-fluorobenzoic acid. To a solution of the obtained carboxamide (1.78 g, 10 mmol) in acetic acid (10 ml), 31% aqueous hydrogen peroxide (2.27 g, 20 mmol) was added and refluxed under heating for 4 hours. After cooling, the reaction mixture was evaporated under reduced pressure, made alkali with 2N aqueous NaOH, extracted with chloroform and dried over Na$_2$SO$_4$. The solvent was evaporated under a reduced pressure to give the title compound (1.61 g; 83%).

$^1$H-NMR(270 MHz, CDCl$_3$) 11.30 (br, 1H), 8.42 (dd, J=8, 2 Hz, 1H), 8.23 (dd, J=6.1 Hz, 1H), 7.46 (td, J=8, 1 Hz, 1H), 7.37 (ddd, J=7, 6, 2 Hz, 1H), 1.49 (s, 9H)

Example 51

N-(2-hydroxy-1,1-dimethyethyl)-2-pyrazinecarboxamide

WSC HCl (1.94 g, 10 mmol) was added to a mixture of 2-pyrazinecarboxylic acid (0.99 g, 8 mmol), 2-amino-2-methyl-1-propanol (0. 80 g, 9 mmol) and HOBt (1.36 g, 10 mmol) in methylene chloride (30 ml), and stirred at room temperature overnight. The reaction mixture was diluted with ethyl acetate and washed with saturated aqueous NaHCO$_3$ and brine, successively, dried over Na$_2$SO$_4$ and concentrated under a reduced pressure. The residue was suspended in methanol (10 ml), added 2N aqueous NaOH to and stirred for 30 minutes. Methanol was evaporated under a reduced pressure, diluted with saturated aqueous NaHCO$_3$ and extracted with chloroform. The extract was washed with with saturated aqueous NaHCO$_3$ and brine, successively, dried over Na$_2$SO$_4$. After the solvent was evaporated, the obtained crystal was washed with hexane and dried to give the title compound (0.27 g; 18%).

$^1$H-NMR(270 MHz, CDCl$_3$) 9.40 (d, J=1.5 Hz, 1H), 8.77 (d, J=2.5 Hz, 1H), 8.53 (dd, J=2.5, 1.5 Hz, 1H), 7.93 (br, 1H), 4.42 (t, J=6.3 Hz, 1H), 3.75 (d, J=6.3 Hz, 2H), 1.44 (s, 6H)

Example 52

N-(2-hydroxy-1,1-dimethyethyl)-4-pyridazinecarboxamide

The title compound (0.31 g; 35%) was prepared by the same method as that described in Example 14, using 4-pyridazinecarsoxylic acid in place of 4-chloro-2-fluorobenzoic acid and purifying the obtained crude product by silica gel chromatography (chloroform/methanol/triethylamine=100/10/1).

$^1$H-NMR(270 MHz, CDCl$_3$) 9.47 (dd, J=2.3, 0.9 Hz, 1H), 9.36 (dd, J=5.3, 0.9 Hz, 1H), 7.80 (dd, J=5.3, 2.3 Hz, 1H), 6.52 (br, 1H), 3.72 (s, 2H), 1.36 (s, 6H)

Example 53

N-(2-hydroxy-1,1-dimethyethyl)-4-pyrazolecarboxamide

A solution of DMF (2 drops) and oxalyl chloride (0.88 g, 4.5 mmol) in methylene chloride (4 ml) was added to a suspension of 4-pyrazolecarboxylic acid (0.50 g, 4.5 mmol) in methylene chloride (6 ml) and stirred at room temperature for 1 hour. The reaction mixture was concentrated and dried under a reduced pressure. To a suspension of the obtained solid in methylene chloride (5 ml) cooled in an ice-bath, 2-amino-2-methyl-1-propanol (1.33 g, 15 mmol) was added. The mixture was stirred at room temperature for 1 hour, added saturated aqueous NaHCO$_3$ to, and concentrated and dried under a reduced pressure. The residue was extracted with warm chloroform and the solvent was evaporated under a reduced pressure. The residue was subjected to silica gel chromatography (chloroform/methanol/triethylamine=100/10/1) to give the title compound (0.37 g, 45%).

$^1$H-NMR(270 MHz, DMSO-d$_6$) 13.0 (br, 1H), 8.1 (br, 1H), 7.9 (br, 1H), 7.14 (s, 1H), 4.93 (t, J=5.9 Hz, 1H), 3.47 (d, J=5.9 Hz, 2H), 1.27 (s, 6H)

Example 54

N-(2-hydroxy-1,1-dimethyethyl)-5-bromo-2-pyrimidinecarboxamide

The title compound was prepared by the same method as that described in Example 14, using 5-bromo-2-pyrimidinecarboxylic acid, which was given by the methods described in J. Chem. Soc., 3129 (1953) and Collect. Czech. Chem. Commun., 37, 1721 (1972), in place of 4-chloro-2-fluorobenzoic acid.

$^1$H-NMR(270 MHz, CDCl$_3$) 8.92 (s, 2H), 8.0 (br, 1H), 4.32 (t, J=6.3 Hz, 1H), 3.75 (d, J=6.3 Hz, 2H), 1.44 (s, 6H)

Example 55

N-(2-hydroxy-1,1-dimethyethyl)-4-bromo-2-fluorobenzamide

The title compound was prepared by the same method as that described in Example 14, using 4-bromo-2-fluorobenzoic acid in place of 4-chloro-2-fluorobenzoic acid.

$^1$H-NMR(270 MHz, CDCl$_3$) 7.94 (t, J=8.3 Hz, 1H), 7.42 (dd, J=8.3, 1.8 Hz, 1H), 7.33 (dd, J=11.4, 1.8 Hz, 1H), 6.7 (br, 1H), 4.22 (t, J=6.3 Hz, 1H), 3.70 (d, J=6.3 Hz, 2H), 1.41 (s, 6H)

Example 56

N-(2-hydroxy-1,1-dimethyethyl)-2-chloro-4-fluorobenzamide

The title compound was prepared by the same method as that described in Example 14, using 2-chloro-4-fluorobenzoic acid in place of 4-chloro-2-fluorobenzoic acid.

$^1$H-NMR(270 MHz, CDCl$_3$) 7.68 (dd, J=8.6, 6.0 Hz, 1H), 7.15 (dd, J=8.4, 2.6 Hz, 1H), 7.06 (ddd, J=8.6, 7.8, 2.6 Hz, 1H), 6.2 (br, 1H), 4.20 (t, J=6. 2 Hz, 1H), 3.71 (d, J=6.2 Hz, 2H), 1.42 (s, 6H)

Example 57

N-(2-hydroxy-1,1-dimethyethyl)-2-fluoro-4-(3-hydroxy-1-propynyl) benzamide

To a solution of N-(2-hydroxy-1,1-dimethylethyl)-4-bromo-2-fluorobenzamide (0.29 g, 1.0 mmol) in triethylamine (5 ml), dichlorobis(triphenylphosphine)palladium (II) (0.035 g, 0.05 mmol), copper(I) iodide (0.009 g, 0.05 mmol) and 2-propyn-1-ol (0.085 g, 1.5 mmol) were added and stirred at 50° C. for 3.5 hours. The reaction mixture was poured into water, extracted with ethyl acetate and dried over Na$_2$SO$_4$. After the solvent was evaporated under a reduced pressure, the residue was subjected to silica gel chromatography (hexane/ethyl acetate=1/2) to give the title compound (0.30 g, 94%).

$^1$H-NMR(270 MHz, CDCl$_3$) 8.00 (t, J=8.2 Hz, 1H), 7.31 (dd, J=8.2, 1.5 Hz, 1H), 7.18 (dd, J=12.6, 1.5 Hz, 1H), 6.8 (br, 1H), 4.51 (d, J=6.4 Hz, 2H), 4.34 (t, J=6.2 Hz, 1H), 3.60 (d, J=6.2 Hz, 2H), 1.78 (t, J=6.4 Hz, 2H), 1.41 (s, 6H)

The structures of the compounds obtained in Example 1 to 57 are as follows:

Example 1

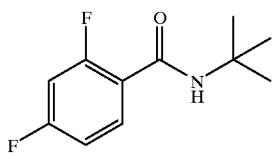

Example 2

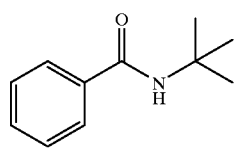

Example 3

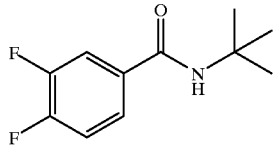

Example 4

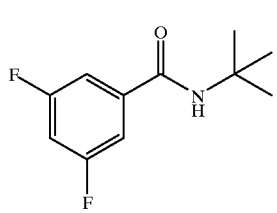

Example 5

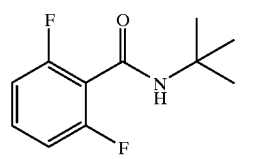

Example 6

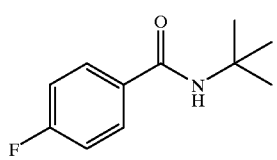

Example 7

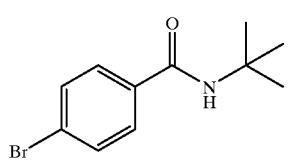

Example 8

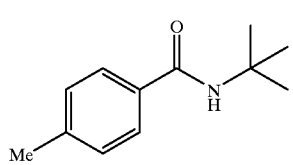

Example 9

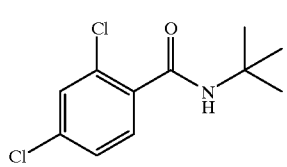

Example 10

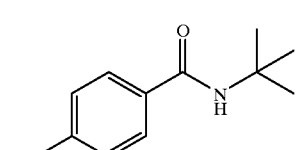

Example 11

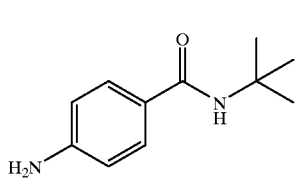

Example 12
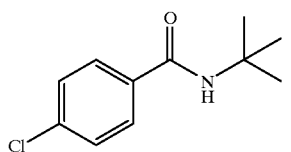
Example 13
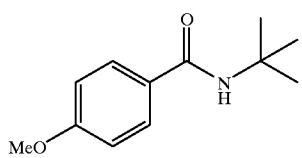
Example 14
Example 15
Example 16
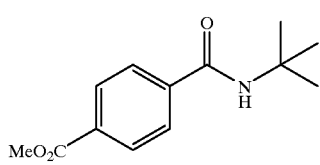
Example 17
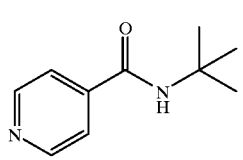
Example 18
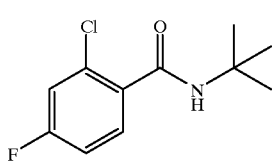
Example 19
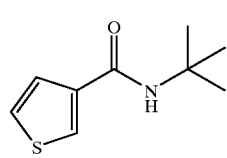
Example 20
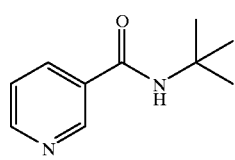
Example 21
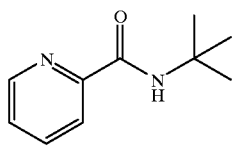
Example 22
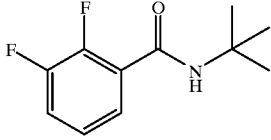
Example 23
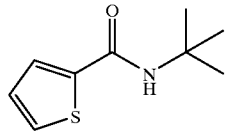
Example 24
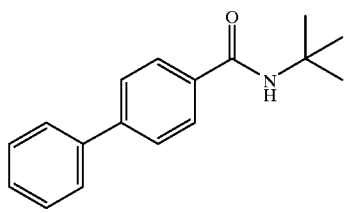
Example 25
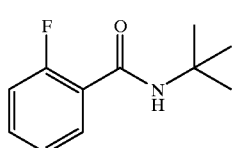
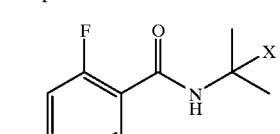
Example 26 X = —CH$_2$F    Example 27 X = —CH$_2$OH
Example 28 X = —CN          Example 29 X = —CONH$_2$
Example 30 X = —CO$_2$Me    Example 31 X = —CH$_2$OMe
Example 32 X = —CHO         Example 33 X = —CH(OH)CH$_3$
Example 34 X = —C(O)CH$_3$  Example 35 X = —CO$_2$H
Example 36 X = —C≡CH        Example 37 X = —CH═CH$_2$
Example 38 X = —CH$_2$CH$_3$
Example 39
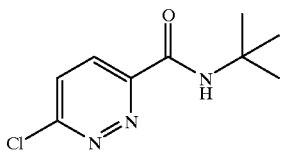

-continued
Example 40
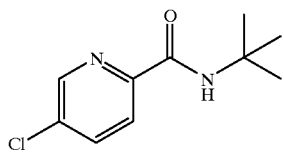
Example 41
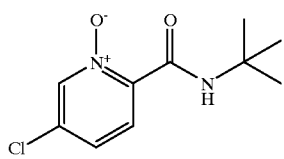
Example 42
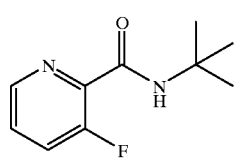
Example 43
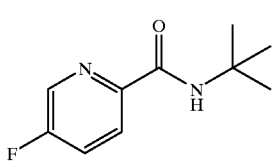
Example 44
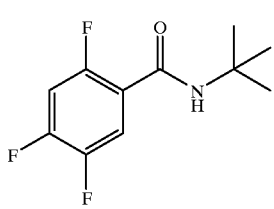
Example 45
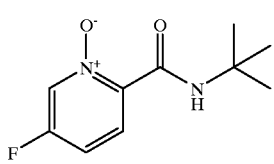
Example 46
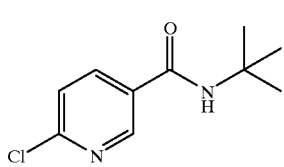
Example 47
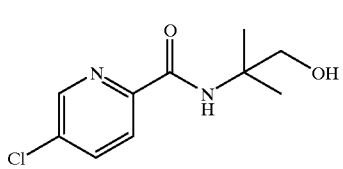
Example 48
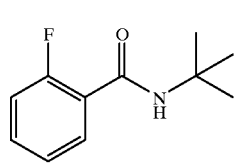
-continued
Example 49
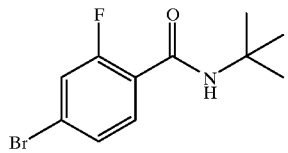
Example 50
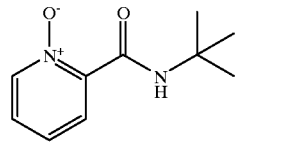
Example 51
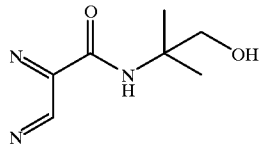
Example 52
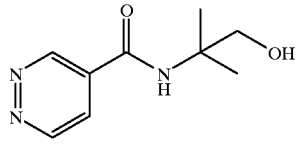
Example 53
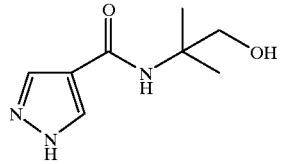
Example 54
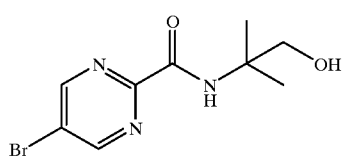
Example 55
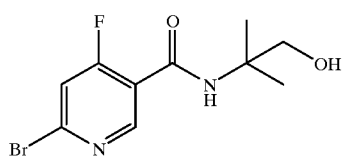
Example 56
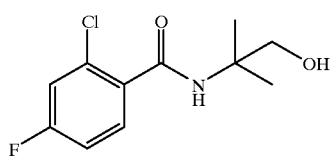
Example 57
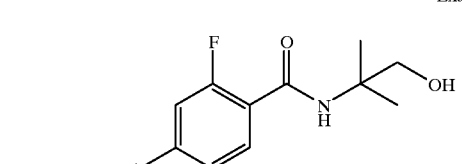

Formulation Example 1
Aqueous Eye Drops

The compound of Example 50 (0.3 g), sodium dihydrogenphosphate (0.56 g), disodium hydrogenphosphate (0.284 g), benzethonium chloride (0.02 g) and sodium chloride (0.28 g) are dissolved in sterile purified water to make the total 100 ml to give aqueous eye drops.

Formulation Example 2
Aqueous Eye Drops

The compound of Example 50 (0.5 g), boric acid (2.0 g), dried sodium sulfite (0.1 g), phenylmercuric nitrate (0.001 g) and citric acid (0.01 g) are dissolved in sterile purified water to make the total 100 ml to give aqueous eye drops.

Formulation Example 3
Aqueous Eye Drops

The compound of Example 50 (1.0 g), boric acid (1.24 g), potassium chloride (0.74 g), thimerosal (0.002 g) and sodium bicarbonate (suitable amount) are dissolved in sterile purified water to make the total 100 ml to give aqueous eye drops.

Formulation Example 4
Aqueous Eye Drops

The compound of Example 50 (1.0 g), boric acid (1.7 g), zinc sulfate (0.1 g) and benzethonium chloride (0.01 g) are dissolved in sterile purified water to make the total 100 ml to give aqueous eye drops.

Formulation Example 5
Oily Eye Drops

The compound of Example 1 (1.0 g) is dissolved or dispersed in peanut oil to make the total 100 ml to give oily eye drops.

Formulation Example 6
Oily Eye Drops

The compound of Example 25 (1.0 g) is dissolved or dispersed in propylene glycol to make the total 100 ml to give oily eye drops.

Formulation Example 7
Oily Eye Drops

The compound of Example 48 (1.0 g), methylparaben (methyl 4-hydroxybenzoate) (0.05 g), propylparaben (propyl 4-hydroxybenzoate) (0.01 g) and β-octyldodecanol (suitable amount) are dissolved or dispersed in propylene glycol to make the total 100 ml to give oily eye drops.

Formulation Example 8
Ophthalmic Ointment

The compound of Example 49 (1.0 g) is dissolved or dispersed in liquid paraffin (5.0 g) and then mixed with white vaseline™ (petrolatum) (94.0 g) homogeneously to give ophthalmic ointment.

Formulation Example 8
Ophthalmic Ointment

The compound of Example 1 (1.0 g) is dissolved or dispersed in plastibase to make the total 100 g to give ophthalmic ointment.

The compounds of formulae 1, 2 and 3 are useful as a medicament for treating retinal neurodegenarative disorders. The retinal neurodegenarative disorders include, for example, retinitis pigmentosa, senile macular degeneration, diabetic retinopathy, glaucoma, traumatic retinal detachment and the like. The compounds of formulae 2 and 3 are also useful as a medicament for treating neurodegenerative disorders (e. g. damage of central nervous system induced by stroke, hypoglycemia, cardiac arrest, perinatal asphyxia, medulla spinalis trauma and the like, and epilepsy, Huntington's chorea, Parkinson's disease, Alzheimer's disease, diabetic neuropathy and the like) and the like.

Retinal outer nuclear cells have been known to be degenerated by the constant white light exposure to albino rats (L. M. Rapp, et al., New York: Plenum, 135 (1980)). Effectiveness of the compounds of formula 1, 2 or 3 or pharmaceutical acceptable salts thereof can be evaluated by their protective action against constant light exposure-induced retinal degeneration in rats. The present invention is embodied by the following experiment.

Experiment 1

Pharmacological Effect Against Constant White Light-induced Retinal Damage

Male Wistar rats (7 weeks old, Charles River Japan Inc.) were purchased and maintained in cyclic light/dark environment (8:00~20:00/light term) for one week, and then placed within the apparatus for constant white light exposure for two days. The constant white light exposure apparatus is a covered breeding box of 1020 mm in length, 425 mm in width, 520 mm in height, which is made of acryl boards and of which all inner side are covered with mirrors. Light was continuously irradiated all the day long (24 hours) using white fluorescent lamp attached to the ceiling of the apparatus. The average illuminance in the apparatus was 174.2 foot candle. After two days in the apparatus, the rats were moved to a darkroom and dark adapted for 1–4 hours. The rats were anesthetized with pentobarbital and placed in a stereotaxic frame. After topical mydriatica was given and electrodes were put on corneal surface, center of the forehead and the lower part of the lobe, the response in active potential of retina to the flash stimulation with fixed energy was determined from the recorded ERG (electroretinogram). The damage of retina was evaluated by the decrease in the amplitude of ERG a-wave which originated from retinal outer nuclear cells (photoreceptors). Test compounds were intraperitoneally injected just before placing the rats into the constant light exposure apparatus and at the same time on the next day to investigate its protective effect.

According to the experimental procedure described above, each test compound in the present invention, which was suspended or dissolved in 0.5% methylcellulose (MC) solution, was intraperitoneally administered twice to three rats in a group at the dose of 50 mg/kg. In the same way, 0.5% MC solution was intraperitoneally administered to the rats in MC group. The rats maintained in 12 hours cyclic light/dark environment were used for normal control group. The protection by the compounds against the retinal damage was represented as % recovery value, and the results were shown in Table 1.

% recovery=(x−z)÷(y−z)×100 x: a-wave amplitude in test compound group
y: a-wave amplitude in normal control group
z: a-wave amplitude in MC group

TABLE 1

Pharmacological effect of tested compounds

| Compounds | % recovery (Mean ± S.E.M.) | N |
| --- | --- | --- |
| The compound of Example 1 | 95.5 ± 12.3 | 3 |
| The compound of Example 6 | 80.1 ± 8.9 | 3 |
| The compound of Example 27 | 45.7 ± 10.1 | 3 |
| The compound of Example 40 | 82.3 ± 25.6 | 3 |
| The compound of Example 47 | 58.2 ± 2.7 | 3 |

Experiment 2
Pharmacological Effect Against Constant White light-induced Retinal Damage The protective effect of the compound of Examples by administration of eye drops was tested by the same method as Experiment 1. The tested compounds were administered immediately before rats were placed within the apparatus for constant white light exposure. Further, the eye drops were administered 3, 6, 9 and 24 hours after and the effect was evaluated.

The compounds of the present invention were dissolved in 0.5% aqueous methylcellulose (MC) solution and each 50 μl of the solution per once was dropped to both eyes of 5 rats, according to the method of Experiment 1. In the same way, 0.5% MC solution was dropped to eyes of the rats in MC group. The rats maintained in 12 hours cyclic light/dark environment were used for normal control group. The protection against the retinal damage was represented as % recovery value, and the results were shown in Table 2.

TABLE 2

Protective effect of tested compounds

| Compounds | Concentration | % recovery (Mean ± S.E.M.) | N |
| --- | --- | --- | --- |
| The compound of Example 1 | 2 mg/ml | 11.6 ± 2.6 | 5 |
| The compound of Example 50 | 10 mg/ml | 19.1 ± 7.5 | 5 |
| The compound of Example 49 | 0.4 mg/ml | 5.1 ± 1.8 | 5 |
| The compound of Example 25 | 1.2 mg/ml | 16.2 ± 3.2 | 5 |
| The compound of Example 48 | 3.2 mg/ml | 15.0 ± 3.7 | 5 |

Experiment 3
Pharmacological Effect Against Constant White Light-induced Retinal Damage The compound of Example 50 was further tested by the same method as Experiment 2.

The compound of the present invention was dissolved in 0.5% aqueous methylcellulose (MC) solution and each 50 μl of the solution per once was dropped to both eyes of 5 rats, according to the method of Experiment 1. In the same way, 0.5% MC solution was dropped to eyes of the rats in MC group. The rats maintained in 12 hours cyclic light/dark environment were used for normal control group. The protection against the retinal damage was represented as % recovery value, and the results were shown in Table 3.

TABLE 3

Protective effect of tested compounds

| Compounds | Concentration | % recovery (Mean ± S.E.M.) | N |
| --- | --- | --- | --- |
| Solvent only | | 0.0 ± 5.7 | 5 |
| The compound of Example 50 | 3 mg/ml | 2.3 ± 3.8 | 5 |
| The compound of Example 50 | 10 mg/ml | 6.9 ± 5.7 | 5 |
| The compound of Example 50 | 30 mg/ml | 17.4 ± 3.9** | 5 |
| The compound of Example 50 | 60 mg/ml | 35.6 ± 2.7** | 5 |

**significant difference from solvent only group (p < 0.01, Dunnett method)

INDUSTRIAL APPLICABILITY

The present invention can provide a medicament for treating retinal neurodegenerative disorders and the like.

What is claimed is:
1. A pharmaceutical composition for treating retinal neurodegenerative disorder comprising a compound of the formula:

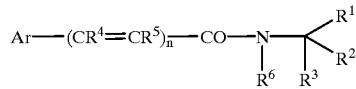

wherein,
Ar is substituted phenyl or substituted or unsubstituted aromatic heterocyclic group, wherein said phenyl group is substituted by a fluorine atom and may be further substituted with substituents; said aromatic heterocyclic group is a 5- or 6-membered aromatic heterocyclic group containing 1 to 3 atoms selected independently from the group consisting of nitrogen atom, sulfur atom, and oxygen atom; and the substituent of the further substituted phenyl group and the substituent on the aromatic heterocyclic group are a halogen atom, a cyano group, a nitro group, an alkyl group, an alkyl group substituted by halogen atom(s), an alkoxy group, and alkoxy group substituted by halogen atom(s), an alkoxycarbonyl group, an alkanoylamino group, an amino group, a phenyl group, an alkylaminocarbonylamino group, an alkoxycarbonylamino group, alkylsulfonylamino group, a carbamoyl group or carbamoyl group substituted by alkyl(s);

n is 0, 1 or 2;

$R^1$ is hydrogen atom, substituted or unsubstituted alkyl, substituted or unsubstituted alkenyl, substituted or unsubstituted alkynyl, alkoxycarbonyl, carbamoyl, alkanoyl or cyano;

$R^2$ and $R^3$ are independently substituted or unsubstituted alkyl; or any two groups of $R^1$, $R^2$ and $R^3$ may be taken together with the carbon atom adjacent thereto to form cycloalkane, or all of $R^1$, $R^2$ and $R^3$ may be taken together with the carbon atom adjacent thereto to form bicycloalkane or tricycloalkane, wherein the cycloalkane, the bicycloalkane and the tricycloalkane may be substituted or unsubstituted, wherein the substituent of the substituted alkyl, the substituted alkenyl, the substituted alkynyl, the substituted cycloalkane, the substituted bicycloalkane and the substituted tricycloalkane is a cycloalkyl group, a heterocyclic group, an alkoxy group, an hydroxy group, a halogen atom, an alkoxyalkoxy group, alkanoyloxy group, an amino group, an alkylamino group, a dialkylamino group, an alkanoylamino group, pyrrolidino group, a piperidino group, a piperazino group, 4-alkylpiperazino group or morpholino group, wherein the heterocyclic group is a 5- or 6-membered aromatic heterocyclic group containing 1 to 3 atoms selected independently from the group consisting of nitrogen atom, sulfur atom, and oxygen atom, or 5- or 6-membered aliphatic heterocyclic group containing 1 or 2 atoms selected independently from the group consisting of nitrogen atom, sulfur atom and oxygen atom;

$R^4$ and $R^5$ are independently hydrogen atom or substituted or unsubstituted alkyl, wherein the substituent of the substituted alkyl is a cycloalkyl group, a heterocyclic group, an alkoxy group, an hydroxy group, a halogen atom, an alkoxyalkoxy group, alkanoyloxy group, an amino group, an alkylamino group, a dialkylamino group, an alkanoylamino group, pyrrolidino group, a piperidino group, a piperazino group, 4-alkylpiperazino group or morpholino group, wherein the heterocyclic group is a 5- or 6-membered aromatic heterocyclic group containing 1 to 3 atoms selected independently from the group consisting of nitrogen atom, sulfur atom, and oxygen atom, or 5- or 6-membered aliphatic heterocyclic group containing 1 or 2 atoms selected independently from the group consisting of nitrogen atom, sulfur atom and oxygen atom;

$R^6$ is hydrogen atom, hydroxy or alkyl;

or a pharmaceutically acceptable salt thereof; and a pharmaceutical carrier.

2. A pharmaceutical composition for treating retinal neurodegenerative disorder according to claim 1, wherein n is 0.

3. A pharmaceutical composition for treating retinal neurodegenerative disorder according to claim 1 or claim 2, wherein Ar is fluorophenyl, 2-pyridyl, 3-pyridyl, 4-pyridyl, pyrazinyl, 3-pyridazinyl, 4-pyridazinyl, 2-pyrimidinyl, 4-pyrimidinyl or 5-pyrimidinyl, wherein the fluorophenyl, the 2-pyridyl, the 3-pyridyl, the 4-pyridyl, the pyrazinyl, the 3-pyridazinyl, the 4-pyridazinyl, the 2-pyrimidinyl, the 4-pyrimidinyl and the 5-pyrimidinyl may be substituted by 1 to 3 halogen atoms and the nitrogen atom of the 2-pyridyl, the 3-pyridyl and the 4-pyridyl may be oxidized.

4. A pharmaceutical composition for treating retinal neurodegenerative disorder according to claim 1 or claim 2, wherein Ar is 2,4-difluorophenyl, 4-fluorophenyl, 2-fluoro-4-chlorpheyl, 2-fluoro-4-bromophenyl, 2-fluoro-4-iodophenyl, 2,4,5-trifluorophenyl, 5-chloro-2-pyridyl, 5-fluoro-2-pyridyl, 3-fluoro-2-pyridyl, 2-chloro-5-pyridyl, 1-oxido-5-chloro-2-pyridyl, 1-oxido-5-fluoro-2-pyridyl, 1-oxido-3-fluoro-2-pyridyl, 1-oxido-2-chloro-5-pyridyl or 6-chloro-3-pyridazinyl.

5. A pharmaceutical composition for treating retinal neurodegenerative disorder according to claim 1, wherein $R^1$ is methyl, ethyl, hydroxymethyl or hydroxyethyl and both $R^2$ and $R^3$ are methyl.

6. A pharmaceutical composition for treating retinal neurodegenerative disorder according to claim 1, wherein $R^6$ is hydrogen.

7. A pharmaceutical composition according to claim 1, comprising a compound of the formula:

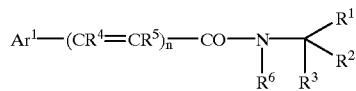

wherein, $Ar^1$ is phenyl substituted by fluorine atom at the 2 or 4 position, which may be substituted by further 1 or 2 halogen atoms, or substituted or unsubstituted 6-membered aromatic heterocyclic group, wherein said 6-membered aromatic heterocyclic group contains 1 to 3 atoms selected independently from the group consisting of nitrogen atom, sulfur atom, and oxygen atom, the substituent on the aromatic heterocyclic group is a halogen atom, a cyano group, a nitro group, an alkyl group, an alkyl group substituted by halogen atom(s), an alkoxy group, an alkoxy group substituted by halogen atom(s), an alkoxycarbonyl group, an alkanoylamino group, an amino group, a phenyl group, an alkylaminocarbonylamino group, an alkoxycarbonylamino group, alkylsulfonylamino group, a carbamoyl group or carbamoyl group substituted by alkyl(s);

n, $R^1$, $R^2$, $R^3$, $R^4$, $R^5$ and $R^6$ are as defined in claim 1;

or a pharmaceutically acceptable salt thereof; and a pharmaceutical carrier.

8. A pharmaceutical composition according to claim 7, wherein n is 0.

9. A pharmaceutical composition according to claim 7 or claim 8, wherein the substituted or unsubstituted 6-membered aromatic heterocyclic group is 2-pyridyl, 3-pyridyl, 4-pyridyl, pyrazinyl, 3-pyridazinyl, 4-pyridazinyl, 2-pyrimidinyl, 4-pyrimidinyl, 5-pyrimidinyl, wherein the 2-pyridyl, the 3-pyridyl, the 4-pyridyl, the pyrazinyl, the 3-pyridazinyl, the 4-pyridazinyl, the 2-pyrimidinyl, the 4-pyrimidinyl and the 5-pyrimidinyl may be substituted by 1 to 3 halogen atoms and the nitrogen atom of the 2-pyridyl, and the 3-pyridyl and the 4-pyridyl may be oxidized.

10. A pharmaceutical composition according to claim 7 or 8, wherein $Ar^1$ is 2,4-difluorophenyl, 4-fluorophenyl, 2-fluoro-4-chlorpheyl, 2-fluoro-4-bromophenyl, 2-fluoro-4-iodophenyl, 2,4,5-trifluorophenyl, 5-chloro-2-pyridyl, 5-fluoro-2-pyridyl, 3-fluoro-2-pyridyl, 2-chloro-5-pyridyl, 1-oxido-5-chloro-2-pyridyl, 1-oxido-5-fluoro-2-pyridyl, 1-oxido-3-fluoro-2-pyridyl, 1-oxido-2-chloro-5-pyridyl or 6-chloro-3-pyridazinyl.

11. A pharmaceutical composition according to claim 7 or 8, wherein $R^1$ is methyl, ethyl, hydroxymethyl or hydroxyethyl and both $R^2$ and $R^3$ are methyl.

12. A pharmaceutical composition according to claim 7 or 8, wherein $R^6$ is hydrogen atom.

13. A method for treating a patient suffering from retinal neurodegenerative disorder, comprising the step of:

administering an effective amount of a pharmaceutical composition to a patient, wherein the pharmaceutical composition comprising a compound of the formula:

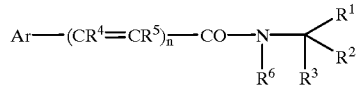

wherein,

Ar is a substituted phenyl or a substituted or unsubstituted aromatic heterocyclic group, wherein said phenyl group is substituted by a fluorine atom and may be further substituted with substituents, said aromatic heterocyclic group is a 5- or 6-membered aromatic heterocyclic group containing 1 to 3 atoms selected independently from the group consisting of nitrogen atom, sulfur atom, and oxygen atom; and the substituent of the further substituted phenyl group and the substituent on the aromatic heterocyclic group are a halogen atom, a cyano group, a nitro group, an alkyl group, an alkyl group substituted by halogen atom(s), an alkoxy group, an alkoxy group substituted by halogen atom(s), an alkoxycarbonyl group, an alkanoylamino group, an amino group, a phenyl group, an alkylaminocarbonylamino group, an alkoxycarbonylamino group, alkylsulfonylamino group, a carbamoyl group or carbamoyl group substituted by alkyl(s);

n is 0, 1 or 2;

$R^1$ is hydrogen atom, substituted or unsubstituted alkyl, substituted or unsubstituted alkenyl, substituted or unsubstituted alkynyl, alkoxycarbonyl, carbamoyl, alkanoyl or cyano;

$R^2$ and $R^3$ are independently substituted or unsubstituted alkyl; or any two groups of $R^1$, $R^2$ and $R^3$ may be taken together with the carbon atom adjacent thereto to form cycloalkane, or all of $R^1$, $R^2$ and $R^3$ may be taken together with the carbon atom adjacent thereto to form bicycloalkane or tricycloalkane, wherein the cycloalkane, the bicycloalkane and the tricycloalkane may be substituted or unsubstituted;

$R^4$ and $R^5$ are independently hydrogen atom or substituted or unsubstituted alkyl; wherein the substituent of the substituted alkyl is a cycloalkyl group, heterocyclic group, an alkoxy group, an hydroxy group, a halogen atom, alkoxyalkoxy group, alkanoyloxy group, an amino group, an alkylamino group, a dialkylamino group, an alkanoylamino group, a pyyrolidino group, a piperidino group, a piperazino group, a 4-alkylpiperazino group or a morpholino group, wherein said heterocyclic group is a 5- or 6-membered aromatic heterocyclic group containing 1 to 3 atoms selected independently from the group consisting of nitrogen atom, sulfur atom, and oxygen atom, or 5- or 6-membered aliphatic heterocyclic group containing 1 or 2 atoms selected independently from the group consisting of nitrogen atom, sulfur atom and oxygen atom;

$R^6$ is hydrogen atom, hydroxy or alkyl;

or a pharmaceutically acceptable salt thereof; and a pharmaceutical carrier.

14. The method for treating a patient suffering from retinal neurodegenerative disorder according to claim 13, wherein the neurodegenerative disorder is retinitis pigmentosa, senile macular degeneration, diabetic retinopathy, glaucoma, traumatic retinal detachment.

15. The method for treating a patient suffering from retinal neurodegenerative disorder according to claim 13, wherein the pharmaceutical composition comprising a compound of N-t-butyl-2,4-difluorobenzamide, N-(2-hydroxy-1,1-dimethylethyl)-2,4-difluorobenzamide, N-(2-hydroxy-1,1-dimethylethyl)-5-chloro-2-pyridinecarboxamide, N-t-butyl-1-oxide-2-pyridinecarboxamide, or a pharmaceutically acceptable salt thereof, and a pharmaceutical carrier.

16. The method for treating a patient suffering from retinal neurodegenerative disorder according to claim 13, wherein the pharmaceutical composition comprising a compound of N-(2-hydroxy-1,1-dimethylethyl)-2,4-difluorobenzamide, or a pharmaceutically acceptable salt thereof, and a pharmaceutical carrier.

17. The method for treating a patient suffering from retinal neurodegenerative disorder according to claim 13, wherein the pharmaceutical composition is administered wherein the compounds are in an amount of from 1 to 1000 mg per day by oral route.

18. The method for treating a patient suffering from retinal neurodegenerative disorder according to claim 13, wherein the pharmaceutical composition is administered wherein the compounds are in an amount of from 10 to 500 mg per day by oral route.

19. The method for treating a patient suffering from retinal neurodegenerative disorder according to claim 13, wherein the pharmaceutical composition is administered wherein the compounds are in an amount of from 0.1 to 500 mg per day by injection.

20. The method for treating a patient suffering from retinal neurodegenerative disorder according to claim 13, wherein the pharmaceutical composition is administered wherein the compounds are in an amount of from 3 to 100 mg per day by injection.

* * * * *